US006821747B2

(12) United States Patent
Bahnson

(10) Patent No.: US 6,821,747 B2
(45) Date of Patent: Nov. 23, 2004

(54) SUPPRESSION OF NON-BIOLOGICAL MOTION

(75) Inventor: Alfred Blalock Bahnson, Pittsburgh, PA (US)

(73) Assignee: Automated Cell, Inc., Pittsburgh, PA (US)

( * ) Notice: Subject to any disclaimer, the term of this patent is extended or adjusted under 35 U.S.C. 154(b) by 0 days.

(21) Appl. No.: 09/904,144

(22) Filed: Jul. 12, 2001

(65) Prior Publication Data

US 2003/0017522 A1 Jan. 23, 2003

(51) Int. Cl.⁷ .............................. C12Q 1/02; C12Q 1/04
(52) U.S. Cl. .......................................... 435/29; 435/30
(58) Field of Search ............................... 435/4, 24, 29, 435/30, 7.1, 7.21, 7.9

(56) References Cited

U.S. PATENT DOCUMENTS

| | | | |
|---|---|---|---|
| 4,161,514 A | * | 7/1979 | Casey |
| 5,866,354 A | * | 2/1999 | Froman |
| 5,916,810 A | | 6/1999 | Jarvik |

OTHER PUBLICATIONS

Nagahata, H., Kociba, G. J. Reiter, J. A., and Couto, C. G., "Analysis of Selected Variables in the Under–Agarose Assay for Chemotactic Responses of Canine Neutrophils", *Am J Vet Res*, 52(6), pp. 965–969, 1991.

Nelson, R. D., Quie, P. G., and Simmons, R. L., "Chemotaxis Under Agarose: A New and Simple Method for Measuring Chemotaxis and Spontaneous Migration of Human Polymorphonuclear Leukocytes and Monocytes", *J Immunol*, 115(6), pp. 1650–1656, 1975.

Nikolai, G., Niggemann, B., Werner, M., Zanker, K. S., and Friedl, P., "Direct and Rapid Induction of Migration in Human CD4+ T Lymphocytes Within Three–Dimensional Collagen Matrices Mediated by Signalling Via CD3 and/or CD2", *Immunology*, 95(1), pp. 62–68, 1998.

Nikolai, G., Friedl, P., Noble, P. B., Niggemann, B., and Zanker, K. S., *Joint Annual Meeting 1995 OGAI/GFI*, 1995.

Rothman, C., and Lauffenburger, D., "Analysis of the Linear Under–Agarose Leukocyte Chemotaxis Assay", *Ann Biomed Eng*, 11(5), pp. 451–477, 1983.

Rupnick, M.A., Stokes, C. L., Williams, S. K. and Lauffenburger, D. A., "Quantitative Analysis of Random Motility of Human Microvessel Endothelial Cells Using a Linear Under–Agarose Assay", *Lab Invest*, 59(3), pp. 363–372, 1988.

Stickle, D. F., Lauffenburger, D. A., and Zigmond, S. H., "Measurement of Chemoattractant Concentration Profiles and Diffusion Coefficient in Agarose", *J Immunol Methods*, 70(1), pp. 65–74, 1984.

Allavena, P., Luini, W., Bonecchi, R., D'Amico, G., Bianchi, G., Longoni, D., Vecchi, A., Mantovani, A., and Sozzani, S., "Chemokines and Chemokine Receptors in the Regulation of Dendritic Cell Trafficking", *Chem Immunol*, vol. 72, pp. 69–85, 1999.

Bleul, C. C., Farzan, M., Choe, H., Parolin, C., Clark–Lewis, I., Sodroski, J., and Springer, T. A., "The Lymphocyte Chemoattractant SDF–1 is a Ligand for Lestr/ Fusin and Blocks HIV–1 Entry", *Nature*, 382(6594), pp. 829–833, 1996.

Boyden, S., "The Chemotactic Effect of Mixtures of Antibody and Antigen on Polymorphonuclear Leucocytes", *J. Exp. Med*, 115, pp. 453–466, 1962.

Crisa, L., Cirulli, V., Ellisman, M. H., Ishii, J. K., Elices, M. J., and Salomon, D. R., "Cell Adhesion and Migration Are Regulated at Distinct Stages of Thymic T Cell Development: The Roles of Fibronectin, VLA4, and VLA5", *J. Exp. Med*, 184(1), pp. 215–228, 1996.

DiMilla, P. A., Stone, J. A., Quinn, J. A., Albelda, S. M. and Lauffenburger, D. A., "Maximal Migration of Human Smooth Muscle Cells on Fibronectin and Type IV Collagen Occurs at an Intermediate Attachment Strength", *J Cell Biol*, 122(3), pp. 729–737, 1993.

Dunn, G. A., "Conceptual Problems with Kinesis and Taxis", In "Biology of the Chemotactic Response" (J. Armitage, and J. Lackie, Eds.). The Press Syndicate of the University of Cambridge, New York, 1990.

Entschladen, F., Niggemann, B., Zanker, K. S., and Friedl, P., "Differential Requirement of Protein Tyrosine Kinases and Protein Kinase C in the Regulation of T Cell Locomotion in Three–Dimensional Collagen Matrices", *J Immunol*, 159(7), pp. 3203–3210, 1997.

Falk, W., Goodwin, R. H., Jr., and Leonard, E. J., "A 48–Well Micro Chemotaxis Assembly for Rapid and Accurate Measurement of Leukocyte Migration", *J Immunol Methods*, 33(3), pp. 239–247, 1980.

Farrell, B. E., Daniele, R. P., and Lauffenburger, D. A., "Quantitative Relationships Between Single–Cell and Cell–Population Model Parameters for Chemosensory Migration Responses of Alveolar Macrophages to C5a", *Cell Motil Cytoskeleton*, 16(4), pp. 279–293, 1990.

Francis, K., Huang, S., Law, P., Ramakrishna, A., Ho, A., and Palsson, B. O., "Human CD34+ Cells Display Coordinated Dependent", *Blood*, 90(10), Abstract 712, 1997.

Friedl, P., Noble, P. B., and Zanker, K. S., "T Lumphocyte Locomotion in a Three–Dimensional Collagen Matrix. Expression and Function of Cell Adhesion Molecules", *J Immunol*, 154(10), pp. 4973–4985, 1995.

(List continued on next page.)

*Primary Examiner*—Christopher R. Tate
(74) *Attorney, Agent, or Firm*—Ansel M. Schwartz

(57) ABSTRACT

A method for analyzing a cell or cells by suppressing non-biological movement. The method includes the steps of placing the cell or cells in a solution having a viscosity enhancement medium. There can be the step of measuring the motility of the cell, or other desired attributes of the cell or cells.

20 Claims, 13 Drawing Sheets

OTHER PUBLICATIONS

Hedrick, J. A., and Zlotnik, A., "Chemokines and Chemokine Receptors in T–Cell Development", *Chem Immunol*, 72, pp. 57–68, 1999.

Lauffenburger, D. A., "Cell Motility: Making Connections Count [News and Views]", *Nature*, 383(6599), pp. 309–391, 1996.

Maheshwari, G., Wells, A., Griffith, L. G., and Lauffenburger, D. A., "Biophysical Integration of Effects of Epidermal Growth Factor and Fibronectin on Fibroblast Migration", *Biophys J*, 76(5), 2814–2823, 1999.

Ware, M. G., Wells, A., and Lauffenburger, D. A., "Epidermal Growth Factor Alters Fibroblast Migration Speed and Directional Persistence Reciprocally and in a Matrix–Dependent Manner", *J Cell Sci*, 111(Pt. 16), pp. 2423–2432, 1998.

Wilkinson, P., "Leucocyte Chemotaxis: A Perspective", In "Biology of the Chemotactic Response" (J. Armitage, and J. Lackie, Eds.), pp. 323–346. The Press Syndicate of the University of Cambridge, New York, 1990.

Lloyd, D. J., "The Problem of Gel Structure", *Colloid Chemistry*, vol. 1, pp. 767–782, 1926.

Terech, P. and Weiss, R. G., "Low Molecular Mass Gelators of Organic Liquids and the Properties of Their Gels", *Chem. Rev.*, 1997, 97, 3133–3159.

Lauffenburger, D., Rothman, C., and Zigmond, S. H., "Measurement of Leukocyte Motility and Chemotaxis Parameters with a Linear Under–Agarose Migration Assay", *J Immunol*, 131(2), pp. 940–947, 1983.

* cited by examiner

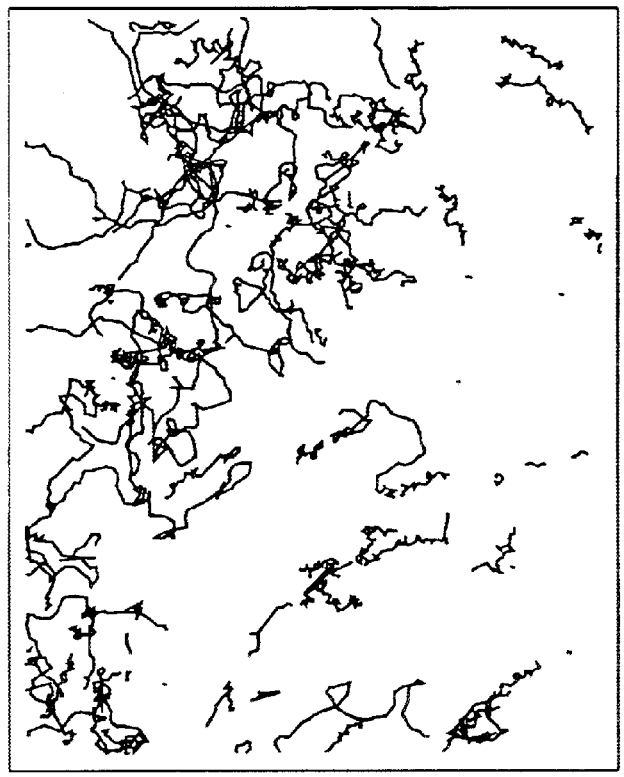
FIG. 7B NO MC
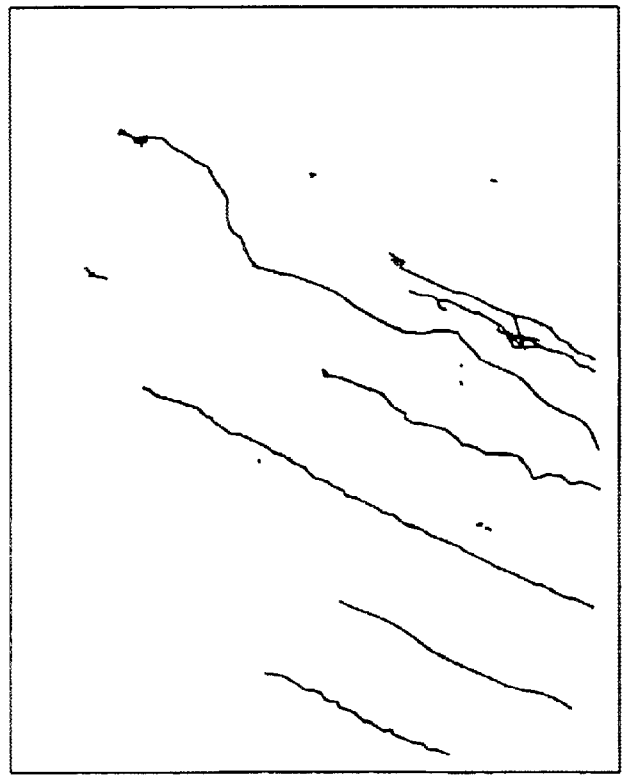
FIG. 7A NO MC

40ul 1.2% MC

40ul 0.4% MC

SUPPRESSION OF NON-BIOLOGICAL MOTION

FIELD OF THE INVENTION

The present invention is related to the suppression of non-biological motion of a cell. More specifically, the present invention is related to the suppression of non-biological motion of a cell having a viscosity enhancement medium, such as methyl cellulose.

BACKGROUND OF THE INVENTION

Cell motility plays an important role in numerous cellular biological processes, for example immune response and modulation, stem cell engraftment in bone marrow transplantation, wound healing, biomaterials compatibility, tissue engineering, tumor metastasis, myocardial angiogenesis and tumor anti-angiogenesis, to name some areas of commercial interest with relevance for improving human health. In all of these cases, the measurement of cell motility in vitro provides a basis for better understanding the biology of the process and for testing the effects of pharmaceuticals or other therapeutic approaches with potential for assisting or inhibiting the process of cell motility.

Time-lapse imaging provides the most direct and informative method for analysis of motility in vitro, particularly for adherent cell types. Velocity and changes in velocity over time, direction of motion, persistence (tendency for motion in one direction), frequency of directional changes, frequency of stopping and starting, time spent in motion and at rest, total distance traveled—these are some of the parameters accessible to the automated time-lapse method of analysis that are not accessible by other means. The capability for dissecting out such features of motion is important for determining mechanisms of interaction of potentially therapeutic compounds, because different aspects of motion can be affected, depending upon the molecular pathway(s) involved (Ware, Wells, and Lauffenburger, 1998).

With time-lapse video, short-lived effects or transient effects of added compounds on motility can be readily quantified through comparison to baseline values up to the moment of compound addition. In cases of chemotactic behavior, the response may arise through signaling of "differential" receptors, i.e. receptors that transmit intracellular signals only when ligand concentration changes (Dunn, 1990). In such cases, the response of the individual cell may depend upon the recent prehistory of the cell; time-lapse analysis reveals such behavior patterns.

Of particular interest to us is the possibility of screening for very short-lived secreted products on the basis of changes in migration patterns or morphology or phenotypic marker expression of cells in the immediate vicinity of transfected or otherwise engineered "secretor cells." Such short-lived products may exist and have important roles in physiological processes, but being short-lived, they would not be readily detectable due to their instability under normal circumstances. Genes for such products could be transfected into "secretor cells" that would express and secrete these products continuously in culture. Changes in motility or other phenotypic indicators of nearby cells would reveal the activity of such compounds. Examples of such compounds might include chemotactic agents, i.e. compounds that induce directed migration in cells. Such compounds guide cells to sites of relevant physiological interactions, for example in coordinating interaction of T cells, dendritic cells, and B cells in peripheral lymphoid tissues for immune response and in guiding neuronal cell synaptic connections during development of the nervous system.

In addition to the analysis of chemotactic responses to short-lived products, as described above, where in situ secretion from living cells would be necessary, we are also interested in analysis of chemotactic responses to more stable compounds, such as chemokines. Such compounds would be released in the vicinity of responding cells by non-biological methods, for example by impregnating gelatin beads or small microvessels or by application of chemotactic compounds to the culture surface.

In some cases, the migratory response to extracellular signaling molecules is linked to changes in cell adhesion molecules and in cell surface markers (phenotype). Moreover, it would be desirable to determine whether specific subpopulations of cells of similar phenotype show similar specific responses in motile behavior toward various stimuli. Linking surface marker phenotype analysis with motile behavior can feasibly be accomplished in parallel with imaging and intelligent image analysis. These goals hold tremendous potential as tools for investigative biology as well as screening of potentially therapeutic compounds.

The present invention addresses the development of capabilities for automated video time-lapse analysis of biological motility of adherent or non-adherent cells of all types. T lymphocytes from peripheral blood are used as a model system here. The category "non-adherent" pertains broadly to cells of the hematopoietic system, including both lymphoid and myeloid lineages. Non-adherent cells can also exist in non-hematopoietic systems, such as freshly isolated myoblasts and certain cell lines (e.g. adapted HeLa (cervical adenocarcinoma) and PC-3 (prostate adenocarcinoma) cells, Colo 205 (colorectal adenocarcinoma), KNRK (normal kidney), RF-1 (gastric adenocarcinoma), Colo 587 (pancreatic adenocarcinoma), and others). Although some hematopoietic cells, most notably monocyte/macrophages and dendritic cells, adhere to tissue culture plastic, most hematopoietic cell types exhibit weak or transient attachment dependent upon added factors, e.g. phytohemaglutinin (PHA), serum components, fibronectin, or immobilized antibodies such as anti-CD3 for T lymphocytes.

Although the non-adherence of blood cells in vivo is implicit, the non-adherent nature in vitro of many types of hematopoietic cells is not so readily accepted. Some investigators hold that T-cells, for example, develop an adherent phenotype upon in vitro activation (consultant, personal communications). Most theories of cell migration and motility require the involvement of molecular attachment of cell adhesion molecules to the surface, for example through integrin-mediated binding to fibronectin (DiMilla et al., 1993; Lauffenburger, 1996; Maheshwari et al., 1999), and there is as yet no satisfactory theory for how non-adherent cells migrate. Nevertheless, observations over the course of numerous experiments, including round-the-clock imaging of CD34+lin-cord blood cells and their progeny, and experiments with naïve and prestimulated peripheral blood T lymphocytes, indicate that hematopoietic cells are highly animated and highly motile. However, it has also become clear that major components of the migratory "behavior" of these cells are non-biological influences of gravity and micro-turbulence, probably due to thermal convection. Convincing evidence for non-biological motion includes observation of dead (propidium iodide positive) cells moving separately in parallel with live cells. Similarly, the movement of beads and particles, the "flocking" or "herding" of live cells for no apparent cause, and finally "forward and reverse" tilting of the entire microscope by less than 3° leave no question that the biological adherence of these cells is relatively weak in comparison to ambient factors such as gravity and turbulence. Yet, as described below, when these ambient factors are controlled, adherence-independent biological motion is clearly evident, and this motion is sensitive to the influence of relevant biological compounds.

Some examples presented in the literature of time-lapse video analysis of hematopoietic cell migration patterns represent, instead, typical examples of environmentally induced "ambient motility" (Crisa et al., 1996; Francis et al., 1997). The cited patterns are similar to those observed repeatedly in a variety of culture vessels with different types of hematopoietic cells, including, even, dead ones. In one of these reported studies, video time-lapse images were used to support an observed arrest of T-cell migration with anti-VLA4 or anti-VLA5 specific antibodies (Crisa et al., 1996). However, the "arrest" of migration observed after antibody addition was timed in each case with the cessation of an initial wave of unidirectional motion lasting for 2.5 hours. In other words, the "arrest" may have occurred without added antibody due to transient and variable ambient motion. In numerous experiments, such ambient motion has been observed as cells initially settle downhill into lower areas of the well. Motion stops when the majority of cells have passed beyond the viewfield. Given such problems, and despite the appeal of video time-lapse imaging for gathering otherwise unobtainable information relating to detailed characteristics of cell migration, there are as yet no validated methods described in the literature for 2 dimensional migration analysis of non-adherent cells.

A method for video time-lapse three-dimensional (3D) analysis of T cell migration has been reported (Friedl, Noble, and Zanker, 1995). This method is based upon the use of 3D collagen gels and does not allow for analysis of motion that is achieved apart from surface adhesion. These authors distinguish 3D from 2D analysis and state, "Onto two-dimensional surfaces coated with ECM components, non-activated peripheral T cells do barely adhere and are therefore incapable of migration. However, the incorporation of these cells into a 3D collagen environment leads to the onset of spontaneous migration; this results in the rapid and persistent tyrosine phosphorylation of FAK, implicating FAK in T cell migration." (Entschladen et al., 1997). This quote confirms the generally held assumption that without adherence, there is no migration. No explanation is offered as to why T cells do not adhere to ECM (extracellular matrix) components coated onto a 2D surface, i.e. tissue culture plastic, and yet T cells do apparently adhere when incorporated into a 3D collagen matrix.

It is suggested that the failure to adequately control ambient motion is the reason why a validated, reproducible method has not yet been put forth for analysis of motion in a 2D environment with non-adherent cells. In the presence of a very slight tilt (less that 30), motion is observed to trend downward, and if slight convection is present, live cells are observed to follow the direction of flow of particles and dead cells. This ambient motion is superimposed upon their active motility. Perhaps upon observing this, other researchers recognize first that there is no strong adherence, and then it may be assumed that all "residual" motion is thermal or biologically irrelevant. However, as described more fully below, clearly relevant biological motion is seen using methyl cellulose in 2D cultures.

Likewise, no method has been presented for analysis of 3D motion in the absence of a solid matrix (e.g. collagen) upon which cells can attach. However, 3D motion among T cells in the absence of a solid support has been observed using methyl cellulose at a concentration of 1.2% (see below). Also, 3D motion in video time-lapse images of myeloid cell subpopulations in typical CFU-GM cultures has been observed using methyl cellulose at a concentration of approximately 0.9%.

Methyl cellulose has been widely applied for the purpose of growing "colonies" of cells. Colonies are small clumps or groups of cells; they are presumed to arise from a single cell, and are used as a measure of "colony forming units" (CFU). The ability of a cell to form a colony is equated with its being a "progenitor" cell, and so CFU type assays are also known as progenitor cell assays. The methyl cellulose allows the formation of a colony to proceed over a one to two-week period in culture without mixing or disruption of the cell positions.

In summary, there are apparently no validated methods in the literature for analysis of migration of T cells or other non-adherent cells on a 2D surface or for analysis of migration in 3 dimensions when there is no solid matrix on which the cells can attach. When methyl cellulose is used, this dissolved compound is not considered to provide attachment surfaces for the cells to adhere to. There may be molecular attachment involved, but there is no apparent requirement for it, because the cells move in medium alone without methyl cellulose where, in the absence of strong ambient motion, they can be observed to "swim" just the same as in methyl cellulose-containing solution. In medium alone, frequently it is difficult to distinguish biological from thermal and other types of ambient motion, and in many cases the ambient motion is not of uniform direction across the viewfield, nor is it constant over time. Therefore, methods to mathematically "correct" for ambient motion will have noise (uncertainty in precision) associated with them, and in many cases this noise will be greater than the magnitude of biological motion. With methyl cellulose, a physical method for suppression of ambient non-biological motion on a 2D surface has been developed when there is no attachment involved.

Interestingly, as reviewed by Wilkinson (Wilkinson, 1990), prior to development of the filter assay (see below), "many beautiful studies" of leukocyte motion were made using video photography and these studies "laid the foundations on which contemporary studies are based." But due to the degree of technical difficulty, these visual methods were abandoned when the Boyden filter assay, now commonly known as the "Boyden chamber" (Boyden, 1962; Falk, Goodwin, and Leonard, 1980) or "Transwell migration assay" (Bleul et al., 1996), was introduced. The vast majority of current motility and chemotaxis investigation is conducted using this method, whereby cells are added to a chamber separated by a membrane from a second chamber containing medium with test compounds. The cells migrate through small well-defined pores into the lower chamber, and after a specified interval, they are counted and compared with background numbers of cells migrating into chambers without added compounds. While an abundance of valuable data has been obtained using the Boyden chamber, this method "also had the drawback that it was now possible to spend a research career studying leukocyte chemotaxis without ever looking at a moving cell or, indeed, knowing its front from its back ¼", according to Wilkinson (Wilkinson, 1990). Also with introduction of the filter method, many of the clear distinctions regarding chemotaxis, chemokinesis, contact guidance, direction reactions, and other forms of locomoter reactions became blurred. Nevertheless, the filter assay is seeing tremendous application in the discovery of a large family of chemotactic compounds known as "chemokines" (Allavena et al., 1999; Hedrick and Zlotnik, 1999), which hold interest for therapeutic application both in terms of the ligands themselves and in terms of their receptors as targets for small drug molecules. The answers to questions about the exact role of each of these chemokines in the host immune response will be better answered with analytical approaches such as described by the present invention.

In the 1970's, the "under-agarose assay" was introduced. An agarose layer was poured over a glass slide to form a gel, then holes were carefully bored and the agarose plugs were removed down to the surface of the glass slide (Nelson, Quie, and Simmons, 1975). Cells were introduced into one hole and chemotactic compounds or control substances could be introduced into the other holes. Over time, the cells were seen to migrate between the agarose and the glass toward a chemotactic compound at a faster rate than toward a neutral control substance. Whereas the Boyden filter assay yields only relative cell numbers, corresponding to relative chemotactic strength, the "under-agarose assay" yielded a distance traveled over time for the cell migration front. This distance was originally compared to the distance traveled by the control front on the other side of the well toward the neutral compound to derive an index of migration. This simplistic approach to migration analysis stimulated valuable mathematical treatment of the problem (Farrell, Daniele, and Lauffenburger, 1990; Lauffenburger, Rothman, and Zigmond, 1983; Nagahata et al., 1991; Rothman and Lauffenburger, 1983; Rupnick et al., 1988; Stickle, Lauffenburger, and Zigmond, 1984), which has provided the mathematical framework for much current thinking in this area. However, the method is subject to variability depending upon how the holes are bored, perhaps due to lifting of the agarose from the glass surface allowing cells to migrate along with channeling fluid rather than through biological motility.

Another method in current use is measurement of the infiltration of lymphocytes into a 3 dimensional collagen gel (Friedl, Noble, and Zanker, 1995; Nikolai et al., 1998; Nikolai G, 1995). Cells are cultured in contact with the gel surface, and after an elapsed time period, cells migrating to a certain depth are counted. This number correlates to cytokinetic activity.

Although all of these methods provide a quantitative measure of migratory activity, their shortcomings leave many aspects of the migratory behavior hidden from the investigator.

SUMMARY OF THE INVENTION

The present invention pertains to a method for analyzing a cell by suppressing non-biological movement. The method comprises the steps of placing the cell in a solution having a viscosity enhancement medium. There is the step of measuring the motility of the cell. Multiple cells can be measured in parallel.

The present invention pertains to a method for analyzing a cell by suppressing non-biological movement. The method comprises the steps of placing the cell in a solution. There is the step of measuring the motility of the cell in the solution when there is no attachment of the cell involved.

The present invention pertains to a method for analyzing a cell by suppressing non-biological movement. The method comprises the steps placing the cell in a solution. There is the step of identifying and quantifying short lived effects or transient effects of added moiety on motility of the cell in the solution.

The present invention pertains to a method for analyzing a cell by suppressing non-biological movement. The method comprises the steps of placing the cell in a solution having a viscosity of about 100–5000 centipose. There is the step of screening for short-lived secreted products from the cell as a function of changes in migration patterns or morphology or phenotypic marker expression of the cell adjacent to transected or otherwise engineered secretor cells or the cells themselves.

The present invention pertains to a method for analyzing a cell. The method comprises the steps of placing the cell in a solution having a viscosity of about 100–5000 centipose. There is the step of linking surface marker phenotype analysis of the cell in the solution with motile behavior of the cell in the solution.

The present invention pertains to a method for analyzing cells. The method comprises the steps of placing the cells in a solution having a viscosity of about 100–5000 centipose. There is the step of linking surface marker phenotype analysis of adherent and non-adherent cells in the solution with motile behavior of the adherent and non-adherent cells in the solution.

The present invention pertains to a method for analyzing a cell. The method comprises the steps of placing the cell in a solution having a viscosity of about 100–5000 centipose. There is the step of performing two-dimensional or three-dimensional migration analysis on the cell in the solution.

The present invention pertains to a method for analyzing a cell. The method comprises the steps of placing the cell in a solution having a viscosity of about 100–5000 centipose. There is the step of analyzing migration of the cell in the solution which occurs without adherence.

The present invention pertains to a method for analyzing a cell by suppressing non-biological movement. The method comprises the steps of placing the cell in a solution. There is the step of controlling ambient motion of the cell in the solution as a reproducible method for analysis of motion in a 2D or 3D environment with non-adherent cells.

The present invention pertains to a method for analyzing a cell by suppressing non-biological movement. The method comprises the steps of placing the cell in a solution. There is the step of analyzing 3D motion of the cell in the solution in the absence of a solid matrix upon which the cell can attach.

The present invention pertains to a method for analyzing a cell by suppressing non-biological movement. The method comprises the steps of placing the cell in a solution. There is the step of suppressing the ambient non-biological motion of the cell in the solution on a 2D surface when there is no attachment involved of the cell.

The present invention pertains to a method for analyzing a cell. The method comprises the steps of placing the cell in a solution having a viscosity of about 100–5000. There is the step of measuring motility of the cell in the solution, where surface attachment by the cell is not utilized.

The present invention pertains to a method for analyzing a cell by suppressing non-biological movement. The method comprises the steps of placing the cell in a solution. There is the step of forming a thin film in the solution whose viscosity resists Brownian and other non-biological sources of motion but does not interfere with active cell biological motion.

The present invention pertains to a method for analyzing a cell by suppressing non-biological movement. The method comprises the steps of placing the cell in a solution. There is the step of adding a protein or other biological or chemical moiety to the solution. There is the step of analyzing the effect of the protein on cell motility, morphology, phenotype, division rate, cell death, or blebbing or disease state.

The present invention pertains to a method for analyzing a cell by suppressing non-biological movement. The method comprises the steps placing the cell in a solution. There is the step of adding a protein to the solution. There is the step of analyzing the protein function regarding the cell using cell motility as an analytical marker.

The present invention pertains to a method for analyzing a cell by suppressing non-biological movement. The method comprises the steps of placing the cell in a solution. There is the step of placing methyl cellulose in the solution to reduce ambient motion of the cell in the solution and eliminate convective motion.

The present invention pertains to a method for suppressing non-biological movement of a cell. The method comprises the steps of placing the cell in a solution. There is the step of forming a layer of methyl cellulose 34 to 137 Um thick in the solution.

The present invention pertains to a method for analyzing a cell by suppressing non-biological movement. The method comprises the steps of placing the cell in a solution. There is the step of using methyl cellulose in the solution for stopping the effects of gravity on the cell in the solution.

The present invention pertains to a method for analyzing a cell by suppressing non-biological movement. The method comprises the steps of placing the cell in a solution. There is the step of using methyl cellulose in the solution for reducing or eliminating the effects of micro-turbulances due to thermal convection in the solution.

The present invention pertains to a method for analyzing a cell. The method comprises the steps of placing the cell in a solution. There is the step of introducing methyl cellulose in the solution for stopping motion of the cells due to mechanical movement of a plate on which the cells are disposed.

The present invention pertains to a method for analyzing a cell. The method comprises the steps of placing the cell in a solution. There is the step of introducing a viscous fluid having a viscosity of about 100–5000 centipose in the solution for stopping or reducing the effects of gravity on the cell.

The present invention pertains to a method for analyzing a cell. The method comprises the steps of placing the cell in a solution. There is the step of introducing a viscous fluid having a viscosity of about 100–5000 centipose in the solution for reducing the effects of micro-turbulences due to thermal convection.

The present invention pertains to a method for analyzing a cell. The method comprises the steps of placing the cell in a solution. There is the step of introducing a viscous fluid having a viscosity of about 100–5000 centipose in the solution for stopping motion of the cells due to mechanical movement of the plate.

The present invention pertains to a method for analyzing a cell by suppressing non-biological movement. The method comprises the steps of placing the cell in a solution. There is the step of using methyl cellulose or any viscous fluid to separate biological motility from ambient motility.

The present invention pertains to a method for analyzing a cell by suppressing non-biological movement. The method comprises the steps placing the cell in a solution. There is the step of measuring biological cell motility with the cell in the solution.

The present invention pertains to a method for analyzing cells. The method comprises the steps of placing the cells in a solution. There is the step of measuring biological cell motility for adherent or nonadherent cells in the solution.

The present invention pertains to a method for analyzing cells. The method comprises the steps of placing the cells in a solution. There is the step of measuring biological motility of both adherent and nonadherent cells using visible and fluorescent images.

The present invention pertains to a method for analyzing a cell. The method comprises the steps of placing the cell in a solution. There is the step of linking a surface marker of the cell in the solution by phenotype analysis with motile behavior. The linking step an include the step of linking a surface marker of the cell in the solution by phenotype with motile behavior.

The present invention pertains to a method for analyzing a cell. The method comprises the steps of placing the cell in a solution. There is the step of measuring swimming vs moving of cells in the solution in a 2D plane, as cells move up into a viscous layer of the solution.

The present invention pertains to a method for analyzing a cell. The method comprises the steps of placing the cell in a solution. There is the step of measuring attachment of the cell to a surface in the solution, by dispensing fluid into the solution and looking for a location where the cell detaches from the surface.

The present invention pertains to a method for analyzing a cell. The method comprises the steps of placing the cell in a solution. There is the step of measuring the effect tilt has on cell motion, by changing the angle a plate is tilted on which the cell is disposed and looking for changes in motion or cell attachment of the cell.

The present invention pertains to a method for analyzing a cell. The method comprises the steps of placing the cell in a solution. There is the step of removing methyl cellulose effects in the solution by mixing the solution and diluting the methyl cellulose.

The present invention pertains to a method for analyzing a cell. The method comprises the steps placing the cell in a solution having methyl cellulose. There is the step of removing the methyl cellulose from the solution. There is the step of treating the cell with a desired material. There is the step of reintroducing the methyl cellulose into the solution.

The present invention pertains to a method for analyzing a cell. The method comprises the steps of placing the cell in a solution having a viscosity of between 100–5000 centipose. There is the step of measuring cell division, morphology, cell phenotype, disease state of the cell, or cell death. There can also be the step of measuring the motility of the cell.

The present invention pertains to a method for analyzing a cell. The method comprises the steps of placing the cell in a solution. There is the step of holding a cell intact for suppressing motility for division detection of the cell in the solution.

The present invention pertains to a method for analyzing a cell. The method comprises the steps of placing the cell in a solution. There is the step of analyzing migratory response of the cell to extracellular signaling molecules linked to changes in cell adhesion molecules and in cell surface markers (phenotype).

The present invention pertains to a method for analyzing cells. The method comprises the steps of placing the cells in a solution. There is the step of identifying specific subpopulations of cells of similar phenotype which show similar specific responses in motile behavior toward various stimuli.

The present invention pertains to a method for analyzing cells. The method comprises the steps of placing the cells in a solution. There is the step of identifying and separating specific subpopulations of the cells based on cell phenotype, morphology, motility, cell proliferation, cell death, or disease state.

BRIEF DESCRIPTION OF THE DRAWINGS

In the accompanying drawings, the preferred embodiment of the invention and preferred methods of practicing the invention are illustrated in which:

FIGS. 7a and 7b show cells swept from a view field in some wells, and not others, respectively, without methyl cellulose present from the period over which the data were analyzed in FIG. 6.

DETAILED DESCRIPTION

Figure 1:
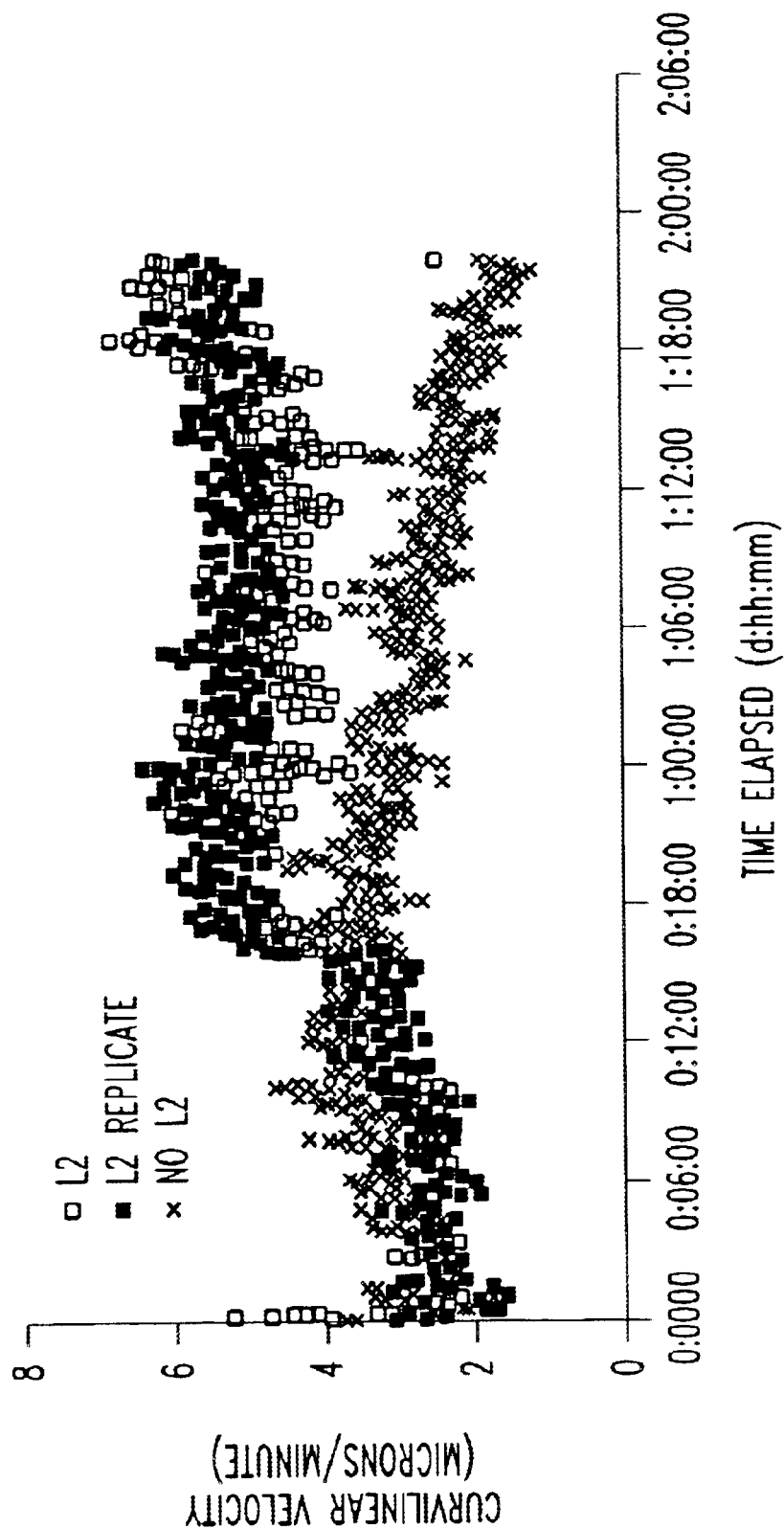
FIG. 1 is plots of average curvilinear velocity for all cell tracks in each viewfield over time demonstrate IL-2 effect on T cell motility.

The present invention pertains to a method for analyzing a cell by suppressing non-biological movement. The method comprises the steps of placing the cell in a solution having a viscosity enhancement medium. There is the step of measuring the motility of the cell. Multiple cells can be measured in parallel.

The viscosity enhancement medium can be methyl cellulose. The viscosity enhancement medium can be hyaluronic acid or chondroitin sulfate or cellulose ester or poly sacharide.

The placing step can include the step of placing the cell in the solution of between 0.1% to 0.2% by total volume of methyl cellulose for 2D analysis of motility. The methyl cellulose solution can have a concentration of between 0.1% and 1.2% methyl cellulose onto cells in culture medium to provide a layer of methyl cellulose-containing medium for 2D analysis of motility. The placing step can include the step of placing the cell in the solution having a viscosity of 100–5000 centipoise. The placing step can include the step of placing cells in solution having a concentration of between 0.3% to 2.5% weight per volume methyl cellulose for analysis of motility in 3D.

The present invention pertains to a method for analyzing a cell by suppressing non-biological movement. The method comprises the steps of placing the cell in a solution. There is the step of measuring the motility of the cell in the solution when there is no attachment of the cell involved.

The present invention pertains to a method for analyzing a cell by suppressing non-biological movement. The method comprises the steps placing the cell in a solution. There is the step of identifying and quantifying short lived effects or transient effects of added moiety on motility of the cell in the solution.

The present invention pertains to a method for analyzing a cell by suppressing non-biological movement. The method comprises the steps of placing the cell in a solution having a viscosity of about 100–5000 centipose. There is the step of screening for short-lived secreted products from the cell as a function of changes in migration patterns or morphology or phenotypic marker expression of the cell adjacent to transfected or otherwise engineered secretor cells or the cells themselves.

The screening step can include the step of screening for short-lived secreted products from the cell as a function of changes in migration patterns or morphology or phenotypic marker expression of the cell adjacent to transfected or otherwise engineered secretor cells.

The present invention pertains to a method for analyzing a cell. The method comprises the steps of placing the cell in a solution having a viscosity of about 100–5000 centipose. There is the step of linking surface marker phenotype analysis of the cell in the solution with motile behavior of the cell in the solution.

The present invention pertains to a method for analyzing cells. The method comprises the steps of placing the cells in a solution having a viscosity of about 100–5000 centipose. There is the step of linking surface marker phenotype analysis of adherent and non-adherent cells in the solution with motile behavior of the adherent and non-adherent cells in the solution.

The present invention pertains to a method for analyzing a cell. The method comprises the steps of placing the cell in a solution having a viscosity of about 100–5000 centipose. There is the step of performing two-dimensional or three-dimensional migration analysis on the cell in the solution.

The present invention pertains to a method for analyzing a cell. The method comprises the steps of placing the cell in a solution having a viscosity of about 100–5000 centipose. There is the step of analyzing migration of the cell in the solution which occurs without adherence.

The present invention pertains to a method for analyzing a cell by suppressing non-biological movement. The method comprises the steps of placing the cell in a solution. There is the step of controlling ambient motion of the cell in the solution as a reproducible method for analysis of motion in a 2D or 3D environment with non-adherent cells.

The present invention pertains to a method for analyzing a cell by suppressing non-biological movement. The method comprises the steps of placing the cell in a solution. There is the step of analyzing 3D motion of the cell in the solution in the absence of a solid matrix upon which the cell can attach.

The present invention pertains to a method for analyzing a cell by suppressing non-biological movement. The method comprises the steps of placing the cell in a solution. There is the step of suppressing the ambient non-biological motion of the cell in the solution on a 2D surface when there is no attachment involved of the cell. The placing step can include the step of placing the cell in the solution of between 1% to 5% by total volume of methyl cellulose and a concentration of between 0.08% and 0.12% of methyl cellulose.

The present invention pertains to a method for analyzing a cell. The method comprises the steps of placing the cell in a solution having a viscosity of about 100–5000. There is the step of measuring motility of the cell in the solution, where surface attachment by the cell is not utilized.

The present invention pertains to a method for analyzing a cell by suppressing non-biological movement. The method comprises the steps of placing the cell in a solution. There is the step of forming a thin film in the solution whose viscosity resists Brownian and other non-biological sources of motion but does not interfere with active cell biological motion.

The present invention pertains to a method for analyzing a cell by suppressing non-biological movement. The method comprises the steps of placing the cell in a solution. There is the step of adding a protein or other biological or chemical moiety to the solution. There is the step of analyzing the effect of the protein on cell motility, morphology, phenotype, division rate, cell death, or blebbing or disease state.

The present invention pertains to a method for analyzing a cell by suppressing non-biological movement. The method comprises the steps placing the cell in a solution. There is the step of adding a protein to the solution. The protein can be a human protein, antibody, growth factor, cytokine, kinase or protease. The protein can be added to the well or transduced or transfected into the cell using known adenovirus or viral methods. There is the step of analyzing the protein function regarding the cell using cell motility as an analytical marker.

The present invention pertains to a method for analyzing a cell by suppressing non-biological movement. The method comprises the steps of placing the cell in a solution. There is the step of placing methyl cellulose in the solution to reduce ambient motion of the cell in the solution and eliminate convective motion.

The present invention pertains to a method for suppressing non-biological movement of a cell. The method comprises the steps of placing the cell in a solution. There is the step of forming a layer of methyl cellulose 34 to 137 Um thick in the solution.

The present invention pertains to a method for analyzing a cell by suppressing non-biological movement. The method comprises the steps of placing the cell in a solution. There is the step of using methyl cellulose in the solution for stopping the effects of gravity on the cell in the solution.

The present invention pertains to a method for analyzing a cell by suppressing non-biological movement. The method comprises the steps of placing the cell in a solution. There is the step of using methyl cellulose in the solution for reducing or eliminating the effects of micro-turbulances due to thermal convection in the solution.

The present invention pertains to a method for analyzing a cell. The method comprises the steps of placing the cell in a solution. There is the step of introducing methyl cellulose in the solution for stopping motion of the cells due to mechanical movement of a plate on which the cells are disposed.

The present invention pertains to a method for analyzing a cell. The method comprises the steps of placing the cell in a solution. There is the step of introducing a viscous fluid having a viscosity of about 100–5000 centipose in the solution for stopping or reducing the effects of gravity on the cell.

The present invention pertains to a method for analyzing a cell. The method comprises the steps of placing the cell in a solution. There is the step of introducing a viscous fluid having a viscosity of about 100–5000 centipose in the solution for reducing the effects of micro-turbulences due to thermal convection.

The present invention pertains to a method for analyzing a cell. The method comprises the steps of placing the cell in a solution. There is the step of introducing a viscous fluid having a viscosity of about 100–5000 centipose in the solution for stopping motion of the cells due to mechanical movement of the plate.

The present invention pertains to a method for analyzing a cell by suppressing non-biological movement. The method comprises the steps of placing the cell in a solution. There is the step of using methyl cellulose or any viscous fluid to separate biological motility from ambient motility.

The present invention pertains to a method for analyzing a cell by suppressing non-biological movement. The method comprises the steps placing the cell in a solution. There is the step of measuring biological cell motility with the cell in the solution.

The present invention pertains to a method for analyzing cells. The method comprises the steps of placing the cells in a solution. There is the step of measuring biological cell motility for adherent or nonadherent cells in the solution.

The present invention pertains to a method for analyzing cells. The method comprises the steps of placing the cells in a solution. There is the step of measuring biological motility of both adherent and nonadherent cells using visible and fluorescent images.

The present invention pertains to a method for analyzing a cell. The method comprises the steps of placing the cell in a solution. There is the step of linking a surface marker of the cell in the solution by phenotype analysis with motile behavior. The linking step an include the step of linking a surface marker of the cell in the solution by phenotype with motile behavior.

The present invention pertains to a method for analyzing a cell. The method comprises the steps of placing the cell in a solution. There is the step of measuring swimming vs moving of cells in the solution in a 2D plane, as cells move up into a viscous layer of the solution.

The present invention pertains to a method for analyzing a cell. The method comprises the steps of placing the cell in a solution. There is the step of measuring attachment of the cell to a surface in the solution, by dispensing fluid into the solution and looking for a location where the cell detaches from the surface.

The present invention pertains to a method for analyzing a cell. The method comprises the steps of placing the cell in a solution. There is the step of measuring the effect tilt has on cell motion, by changing the angle a plate is tilted on which the cell is disposed and looking for changes in motion or cell attachment of the cell.

The present invention pertains to a method for analyzing a cell. The method comprises the steps of placing the cell in a solution. There is the step of removing methyl cellulose effects in the solution by mixing the solution and diluting the methyl cellulose.

The present invention pertains to a method for analyzing a cell. The method comprises the steps placing the cell in a solution having methyl cellulose. There is the step of removing the methyl cellulose from the solution. There is the step of treating the cell with a desired material. There is the step of reintroducing the methyl cellulose into the solution.

The present invention pertains to a method for analyzing a cell. The method comprises the steps of placing the cell in a solution having a viscosity of between 100–5000 centipose. There is the step of measuring cell division, morphology, cell phenotype, disease state of the cell, or cell death. There can also be the step of measuring the motility of the cell.

The present invention pertains to a method for analyzing a cell. The method comprises the steps of placing the cell in a solution. There is the step of holding a cell intact for suppressing motility for division detection of the cell in the solution.

The present invention pertains to a method for analyzing a cell. The method comprises the steps of placing the cell in a solution. There is the step of analyzing migratory response of the cell to extracellular signaling molecules linked to changes in cell adhesion molecules and in cell surface markers (phenotype).

The present invention pertains to a method for analyzing cells. The method comprises the steps of placing the cells in a solution. There is the step of identifying specific subpopulations of cells of similar phenotype which show similar specific responses in motile behavior toward various stimuli.

The present invention pertains to a method for analyzing cells. The method comprises the steps of placing the cells in a solution. There is the step of identifying and separating specific subpopulations of the cells based on cell phenotype, morphology, motility, cell proliferation, cell death, or disease state.

In the operation of the invention, methyl cellulose is a common name for solutions of methyl cellulose in cell culture medium. Methyl cellulose added to medium increases the viscosity so that convection and mixing are greatly suppressed at the level of the cells.

Stem Cell Technologies in Vancouver has a line of products that incorporate methyl cellulose for the purpose of colony assays. These products are generally known under the trade name MethoCult. The line includes the "base" to which other components may be added. This base consists of a sterile 2.6% solution of methyl cellulose in Iscove's Modified Dulbecco's Medium (IMDM). The specification of the methyl cellulose used is as follows: a 2% aqueous solution at 20° C. has a viscosity of 4,000 centipoises. IMDM is one of several varieties of nutrient solution used to grow cells.

The MethoCult "base" has been utilized for studies with T cell migration analysis. USP Grade has the same viscosity specification, as for example catalog # M0512 from Sigma-Aldrich in St. Louis, Mo. The Sigma catalog lists 5 different grades of viscosity of 2% solutions at 20° C.: from 15 centipoises through 25, 400, 1,500 to 4,000 centipoises. The methyl cellulose should have a viscosity of 4,000 centipoises in aqueous solutions at 20° C.

Practical ranges of concentration that work for the purpose of migration analysis of nonadherent cells are shown to lie within approximate concentrations of between 0.1% and 1.2% when the methyl cellulose solution is layered onto cells at the bottom of the well. For adherent cell motility, methyl cellulose is not necessary, but it would be necessary for chemotaxis determination. It is possible that formulation of higher methyl cellulose concentrations up to approximately 2.5% would become advantageous for certain layering purposes. For example, when exchanging the medium above a thin methyl cellulose solution layer, the resistance to dilution might be better with higher methyl cellulose concentrations, i.e. it could be more durable than lower concentrations.

When using a layer of methyl cellulose solution added to cells, the volume of methyl cellulose solutions needed to prevent ambient migration of non-adherent cells depends upon the size of the containers. For 96 well plates, where typically 100 ul volumes of medium are used, the volume of methyl cellulose required can be as low as 1 ul. For general purposes, 4 to 5 ul have been used routinely in 96 well plates. It can be generalized that between 1 to 5% of the total volume is effective for the methyl cellulose solution. This can be applied to any size of sample wells from 6 well plates to 1536 well plates, and plates of even higher density (9600+) well plates. In some circumstances, much larger volumes might be advantageous, as when investigating the 3 dimensional motility of non-adherent cells, or perhaps when using large vessels where convection and mechanical mixing would disrupt the thin layer. Adherent cells are cells that strongly attach to a surface such as the well bottom. These cells are not significantly effected by methocel or the influence of particles in a well. Cells that are considered nonadherent, such as stem cells, have minimal attachment or cyclical attachment to a surface. This minimal attachment is easily overcome by other forces such as gravity or particle movement in the fluid environment. If the viscosity of the fluid environment is slightly increased, the cells move freely on the bottom of the well, with no effect from motion of particle or dead cells in the same environment. The motion of nonadherent cells can be due to minimal attachment and reattachment of the cell to the surface or, under certain conditions, the cells will swim. That is, the cells will move without any attachment to the surface. This can be accomplished if the viscosity of the medium is high enough. In that case, the nonadherent cells will actually swim up, off the surface of the well in the more viscous fluid.

The rationale for using small volumes of methyl cellulose was based upon a number of expectations. First was the expectation that the higher specific gravity of concentrated solution in comparison to medium would result in rapid settling of the added material to the bottom of the well and that the high viscosity of the solution would help to maintain the concentration as it settled through the medium. Next was the expectation that upon reaching the bottom, the material would spread, still undiluted, into a thin film whose viscosity would resist Brownian and other non-biological sources of motion such as the gravitational downhill trend of cells on tilted surfaces and thermal convection. Furthermore, this spreading was observed not to significantly push or sweep cells along in front of its spread. Finally, the viscosity was not expected to interfere with active cell-biological motion. The latter expectation was based upon previous observations of CFU-GM colonies. (The CFU-GM colony assay is prepared in a homogeneous solution of methyl cellulose (approximately 0.9%)). In these CFU-GM time-lapse images, alongside colonies of non-motile cells, were other cells migrating without apparent interference through the methyl cellulose in 3 dimensions. Some cell phenotypes are seen to move extremely rapidly. These observations dispel a presumed requirement for surface attachment in the mechanism of motility used by these hematopoietic cells.

It is more convenient to mix the methyl cellulose into a homogeneous solution with the cells and culture medium prior to or during the cell plating step. In this case, the final concentration range is restricted to between approximately 0.1% to 0.2% final methyl cellulose concentration. At lower concentrations, ambient motion is not suppressed, and at higher concentrations, actively motile cells can lift off from the surface and migrate in 3 dimensions out of focus into the overlying medium.

The motion of a cell off of the bottom of a well is observed as a cell that moves out of focus in that plane of focus in a well. For 3 dimensional analysis, a focal stack at a given position is preferred. The stage moves to a position at a specified time and takes a number of images at different focal planes, usually 5 to 10 images. The images are processed and cells that are in focus are identified, by characteristics such as cell area. Cells that are out of focus will appear larger than cells in focus. The motion in 3D is accomplished by tracking cells that are in focus through the focal planes vs time.

Methyl cellulose and other viscosity enhancing compounds in solution provide an environment for cell culture that is fundamentally different from the environment produced by gels, such as the agarose gel used in the "under-agarose assay" (Nelson, Quie, and Simmins 1975) or collagen gels used in the 3D collagen gel assay (Friedl, Noble, and Zanker 1995). Gels are "easier to recognize than to define" (Jordon Lloyd, D. Colloid Chemistry; Alexander, J., Ed.; The Chemical Catalog Co.: New York, 1926; Vol. 1, p767), but may generally be recognized by having 1) "a continuous structure with macroscopic dimensions that is permanent on the time scale of an analytical experiment and (2) is solid-like in its Theological behavior" (Pierre Terech and Richard G. Weiss, Low Molecular Mass Gelators of Organic Liquids and the Properties of Their Gels. Chem. Rev., 97 (8), 3133–3160, 1997.) The molecules in a gel are generally cross-linked in a complex, three-dimensional network that immobilizes the liquid component, so that even though the liquid component, e.g. water, may account for over 99% of the weight of the gel, the "solidlike" behavior conveys a property such that no discernable flow or change is observable over long periods of time. Common gels used in biological studies are gelatin, a protein, and agarose, a type of polysaccharide. These gels are formed by dissolving the solid gelator molecules in warm water; upon cooling, inter-molecular cross-linking occurs and a solidlike state is attained at temperatures below the "gelation" temperature. In this case, the process is reversible and such gels may be redissolved by heating to the "melting" temperature. Gels may also be formed by chemical polymerization of smaller subunits under suitable conditions, such as the forming of polyacrylamide gels for protein or DNA analysis or the forming of collagen gels upon pH adjustment of a collagen solution. The polymerization process may or may not be reversible. As in the case of hard-boiled eggs, a third process for forming a gel is the irreversible denaturation of soluble protein.

Clarification of the distinction between a gel and a viscous solution is necessary for two reasons. First, because the present invention does not rely upon the "solidlike" property of a gel to control ambient motion. Instead, the control of viscosity is distinguished by maintaining a liquid state in which cells are free to move in any direction at any time without restriction by, or dependence upon, solidlike linkages or networks. Therefore the present invention reveals migration without requirements for attachment or support and without the interference of a matrix that could confine movement to channels or other small interruptions or openings within a complex network. For this reason, the present invention provides a highly suitable environment for observing and analyzing directional characteristics of cell migration and the effects of compounds upon such directional behavior. Secondly, the distinction is important because gels may be used to confine compounds for the purpose of analysis of the effects of such compounds on cells in the nearby vicinity. For example, a compound may be impregnated within a gel that has been cooled or polymerized into the solidlike state. A small volume of such material can be introduced into the cell culture for the purpose of analysis of the effects of the impregnating compound on nearby cells. In the present invention, the analysis of these cells may involve control of ambient motion in the vicinity of the gel in order to prevent disruption of a concentration gradient that becomes established as the compound diffuses out from the impregnated gel into the surrounding medium. Control of micro-convection using for example methyl cellulose, permits the establishment of a stable gradient while permitting free motion of the cells upon which the gradient is producing stimulatory or inhibitory effects.

One test of methyl cellulose included a major goal for development of an automated assay for motility: the assay must be sensitive to changes in motility brought about by cytokines that are known to stimulate T cells.

Lymphocytes were isolated from freshly drawn venous blood containing acid citrate dextrose anticoagulant by density gradient centrifugation over Lymphoprep (Gibco/BRL). Cultures were depleted of adherent monocytes by incubation (37° C., 5% $CO_2$, humidified) in tissue culture flasks in complete medium consisting of 10% fetal bovine serum (FBS, Gibco/BRL), in RPMI containing 200 mM 1-glutamine, penicillin and streptomycin. The non-adherent cells from monocyte-depleted cultures were stimulated for three days in complete medium containing 5 ug/ml phytohemagluttinin (PHA, Sigma). PHA stimulated cells were then washed and resuspended in complete medium containing 5 ng/ml interleukin-2 (IL-2, R&D Systems). After at least 2 days of pre-stimulation in IL-2, cells were washed three times, resuspended in complete medium, and "rested" by overnight incubation prior to analysis of response to cytokine mixtures.

For plating into 384 well plates, rested cells were suspended in mixtures of fresh medium containing cytokines at indicated concentration(s) with cells at a density (4 to $5 \times 10^{4}$/ml) such that approximately 1200 to 1500 cells were seeded in 30 ul into each well of the 384-well plate. Preliminary experiments were performed using 100 ul of cell suspension at similar cell densities in 96 well plates as described in the text. For these experiments, methylcellulose (2.6% stock in IMDM, catalog #4100, Stem Cell Technologies, Vancouver, BC) was diluted in complete medium (½, unless otherwise indicated) and was added to the well as a small volume (1–4 ul) after cells had settled to the bottom surface. For routine assay, methyl cellulose was mixed homogeneously with the cell suspension at a final concentration of 0.2% (1/12 dilution of stock). Propidium iodide (2 ug/ml) was added for identification of dead cells. Uniform settling of cells was assisted by brief centrifugation (2 min @ 500 g) of the plate in a micro-titer plate carrier.

Visible and fluorescent time-lapse images were acquired at 1.5 minute intervals using a Nikon TE-300 epi-fluorescence inverted microscope with an automated stage that returns precisely to a pre-selected viewfield centrally located within each well. The digital camera is a cooled CCD SenSys (Photometrics). Magnification was through a 10× objective with an 0.6× high resolution reduction lens (Diagnostic Instruments). The z-coordinate settings (focus) were determined at the outset of each experiment and automatically reset for each well position throughout the experiment. Fluorescence was obtained using a mercury or xenon source lamp with a 555 nm single band exciter filter (Chroma #86555, Chroma Technology Corp.), a Sedat Quad multiband beamsplitter (Chroma #86100) and a 4 color emission filter (Chroma #84101). Fluorescence exposures were typically 250 msec. The system employs an customer designed incubated chamber that seals on top of the movable heated stage and maintains temperature (37° C.), humidity (>95%) and CO2 (5%) throughout the experimental period. Generally, experiments were performed in triplicate groups using up to 22 wells within a group and with each group being imaged continuously for one hour or more before switching to the next group in a cycling manner over periods of up to three days. Custom software allows the operator to step through selection of imaging sites, to assign them to groups, and to select variables for exposure settings, binning, gain, scan intervals, and so forth. Images are stored as 8 bit with JPEG compression and 2×2 binning.

A variety of mathematical algorithms are used to detect live objects and suppress background artifacts within each gray scale image through a process of image enhancement, topological analysis and object contour extraction. Segment shapes which satisfy morphological and topological criteria are used to form final binary object images for both the visible and fluorescent image sets. Fluorescent objects, representing dead cells, are subtracted from the visible objects where the two coincide and the resulting binary image set is used to develop the motion dynamics of live objects. A track represents the path of migration of an object; multiple tracks are built automatically based upon probability fields for assigning links between objects from one image to the next. Statistical parameters are developed from these links that summarize the motion analyzed in terms of velocity, direction of travel, tendency toward a straight line, frequency and magnitude of changes in direction along a smoothed curve, and percentage of objects moving within the entire view-field or region of interest. These statistics may be further averaged over time and between imaging sites to assay and compare the effects of added compounds on migratory rates. Frequently presented parameters include "curvilinear velocity" calculated as the average over twenty scans of the distance per scan traveled by the tracked cell divided by the time between scans. For purposes of detecting ambient motion, "straight line velocity" is used; this represents the straight line distance from the center of a tracked object between one image and another image twenty scans later divided by the elapsed time over twenty scans. Since this parameter is a vector, its average among the many cells in each view-field tends toward zero (0) when the directions are random because vectors in opposite directions cancel each other. However, when ambient motion is present, the additive effect of many cells moving in a similar direction is readily apparent as an increase in this parameter.

The more important mathematical parameters calculated each cell include:

$Vinst_k(i)$—instantaneous speed of a track at a specific scan number $Vavg\_inst_k(i)$—instantaneous speed of a smoothed track at a specific scan number Vcl—curvilinear velocity, characteristics of the whole track Vsl—straightline velocity, characteristics of the whole track Vavg—curvilinear velocity of smoothed track, characteristics of the whole track Linearity—the measure of how straight cell is moving, characteristics of the whole track.

Straightness—the same meaning as Linearity but the smoothed track is used instead of real. Allows to exclude the fast direction fluctuations from measurements ALHmean—the mean beating amplitude, the measure of oscillating component of cell movement. Characteristics of the whole track.

ALHmax—the maximum beating amplitude, the measure of oscillating component of cell movement. Characteristics of the whole track BCF—beat cross frequency, the measure of oscillating component of cell movement. Characteristics of the whole track Circular Radius—measure of circular component of the cell motion If he track passes some criteria, it is approximated by the circle (using least square fit) and the radius of this circle becomes the Circ. Radius. Characteristics of the whole track Referring now to the drawings wherein like reference numerals refer to similar or identical parts throughout the several views, and more specifically to FIG. 1 thereof, there is shown the results of analysis of T cell motility in response to stimulation by the cytokine, interleukin-2 (IL-2). A cytokine is a type of protein.

For this experiment, prestimulated cells (3 days PHA, 2 days IL-2; see above) were washed and resuspended in complete medium and were plated into a 96-well plate using approximately 5,000 cells per well. After the cells had settled to the surface, 4 ul of methyl cellulose solution (Stem Cell Technologies #H4230) was added and the plate was installed on the automated stage of the inverted microscope and imaging was begun (time=0). Imaging continued during the initial 15 hour nonstimulatory "rest" period in medium without cytokine, at which time IL-2 was added (final concentration 100 ng/ml) and imaging was resumed. Curvilinear velocity (Vcl) is shown for duplicate wells to which IL-2 was added (upper, diamonds and squares) in comparison to a control well to which no IL-2 was added (lower, triangles). The added IL-2 induced an immediate increase in T cell velocity that was sustained throughout the subsequent 24 hour period shown here.

Figure 2A:
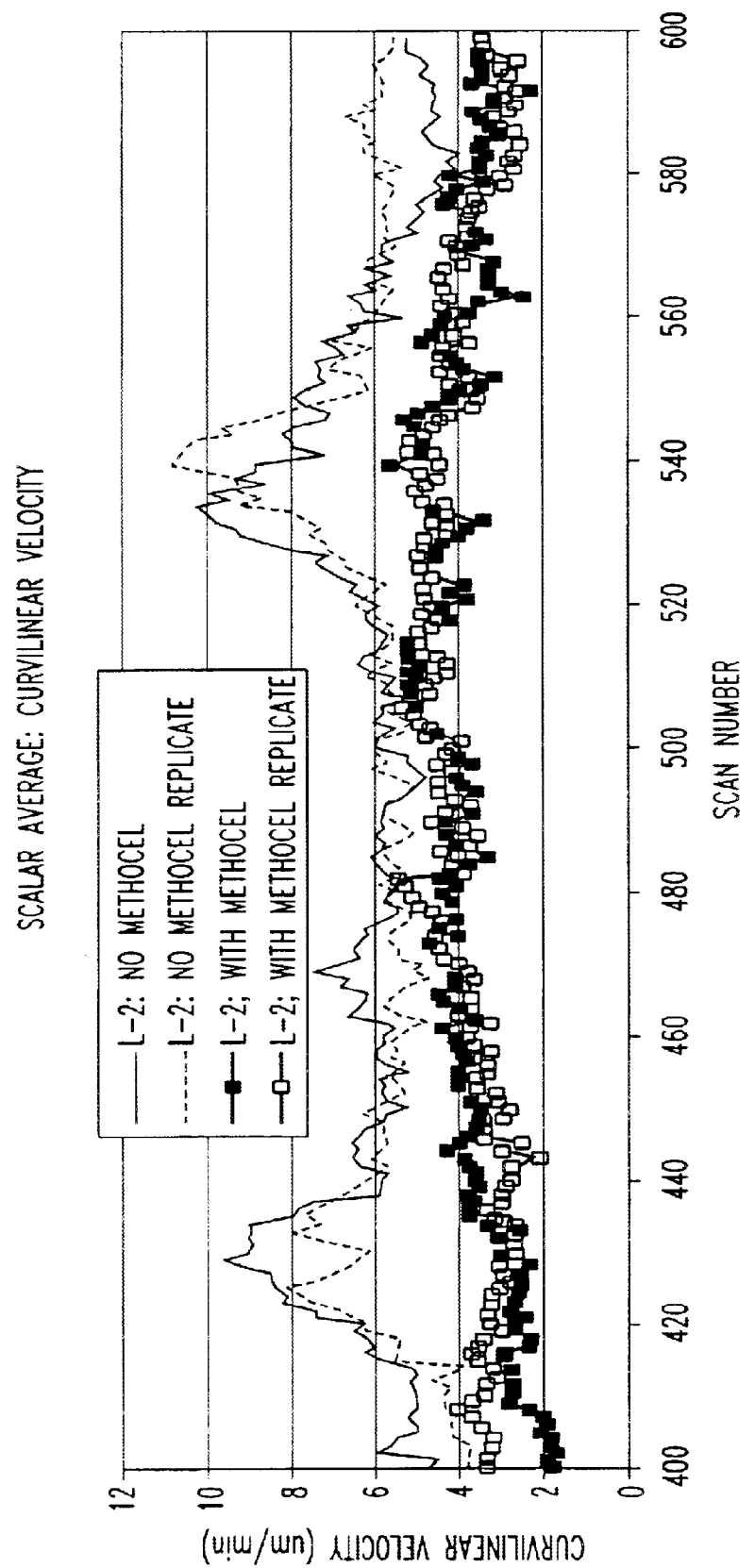
FIGS. 2a and 2b are a comparison of average curvilinear velocity (Vcl), a scalar quantity, with straight line velocity (Vsl), a vector, for cells in wells with and without methyl cellulose.
Figure 2B:
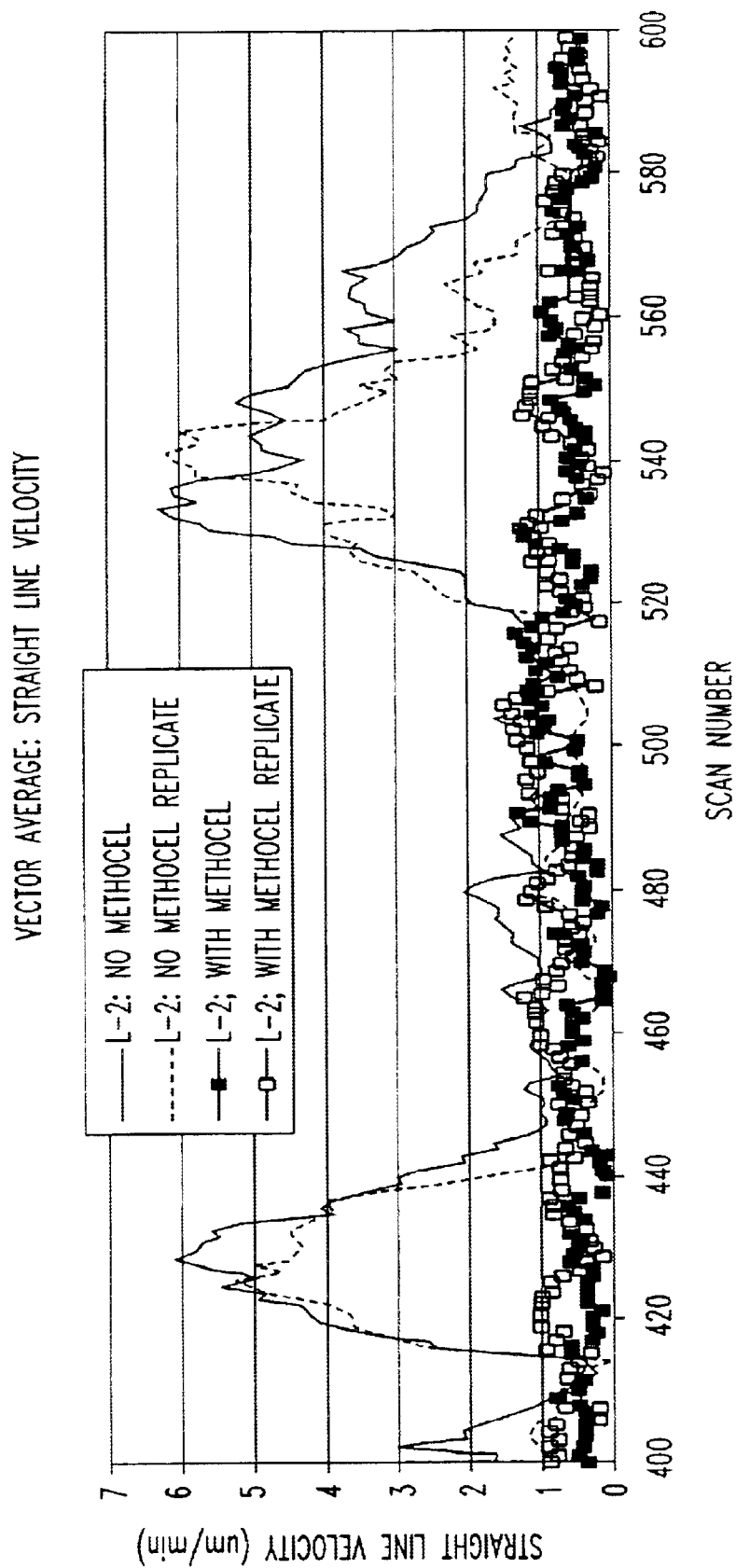

In previous experiments, motility response was often obscured by large unpredictable fluctuations. Abbreviated analysis of control wells without methyl cellulose from this experiment indicated that such fluctuation was occurring in this experiment also (FIG. 2). FIGS. 2A and 2B compare average curvilinear velocity (Vcl) with straight line velocity (Vsl) for cells in wells with and without methyl cellulose. Vcl is a scalar quantity representing the average magnitude of velocities of all cells in the view, whereas Vsl averages both the magnitude and the direction of cells moving in the view. Vsl is a useful indicator of ambient motion because it becomes large when cells move in a similar direction and small when cells move randomly. Ambient motion is characterized by fluctuations over time of cells moving in a similar direction resulting in variable large Vsl values as shown here for samples without methyl cellulose (FIG. 2b, top four curves). On the other hand, samples with methyl cellulose exhibit random motion as characterized by consistently low Vsl values throughout the analysis period. Only 200 scans are shown (~5 hours) and only ¼ of the original 10× image was analyzed in order to reduce processing time. Ambient motion is observed if no methylcel is present. Particles and dead cells move together as though they were motile. A live cell in a well will also move along with the particles. This motion, ambient motion, is caused by fluid motion in the well. The fluid motion is produced by changes in temperature setting up convection, or micro turbulences that sweep smaller particles around, pulling the cells along. If the plate is moved, mechanically, the particles, since they are not the same density as the fluid will move at different rates than the fluid and the cells. This motion will also be seen, it's ambient motion. If the plate is tilted, the more dense particles will move down hill, again causing the cells to move along with the particles. With the correct concentration of methocel present, the turbulence is minimized, and motion due to mechanical motion of the well/cell does not cause particles to move around. Since it is possible to observe wells with and without methocel in the same experiment, the effect that ambient motility has on cell 'biological' motility can also be detected. If the plate is tilted, the particles and dead cells will stay put, giving the user a method to measure the effect that gravity has on the true cell motion, not influenced by ambient motion. The amount of tilt is also a measure of attachment of the cell in the environment. Other changes in the environment, such as a surface treatment in the well or an addition of a protein in the fluid can be studied to see the effect of cell attachment in a tilted well, independent of the effects of ambient motility.

These data demonstrate that methyl cellulose provides the desired effects of reducing ambient motion without preventing biological motion, including responsiveness to IL-2.

Having demonstrated the potential usefulness of methyl cellulose, the effective concentration range was examined. In order to determine the minimum methyl cellulose concentration at which ambient motion suppression is effective, a dilution series of methyl cellulose in medium was prepared and added to a series of wells in a 96 well plate. As in the first experiment, a volume of 4 ul of methyl cellulose was used. Larger volumes were also tested in order to provide assurance that dilution of smaller volumes was not resulting in inaccuracy in the assumed concentration at the surface level and to compare the durability of thinner versus thicker methyl cellulose layers. Dilution is expected due to mixing at the time of layering upon the bottom and due to diffusion over the course of the experiment. The results for this experiment are shown in FIG. 3. In each case, Vsl is plotted over the course of the 15 hour experiment (x axis expressed in scans, where each scan is approximately 3 minutes). Methyl cellulose dilutions of $\frac{1}{128}$ (0.01% methyl cellulose) and $\frac{1}{64}$ (0.02% methyl cellulose) were not effective, but some suppression of ambient motion is observed at $\frac{1}{32}$ dilution (0.04% methyl cellulose) for all volumes (FIG. 3A–D). At $\frac{1}{16}$ dilution (0.08% methyl cellulose), a 4 ul volume is somewhat effective for about 8 hours; a 4 ul volume at $\frac{1}{8}$ dilution (0.15% methyl cellulose) is effective for at least 15 hours (FIG. 3A).Presumably the increased ambient motion at $\frac{1}{16}$ dilution after 8 hours results from dilution by diffusion and from convective "currents" that may be set up due to heating differentials within a well; these same currents at the culture surface are likely to cause ambient motion of cells, but methyl cellulose prevents this.

Figure 3A:
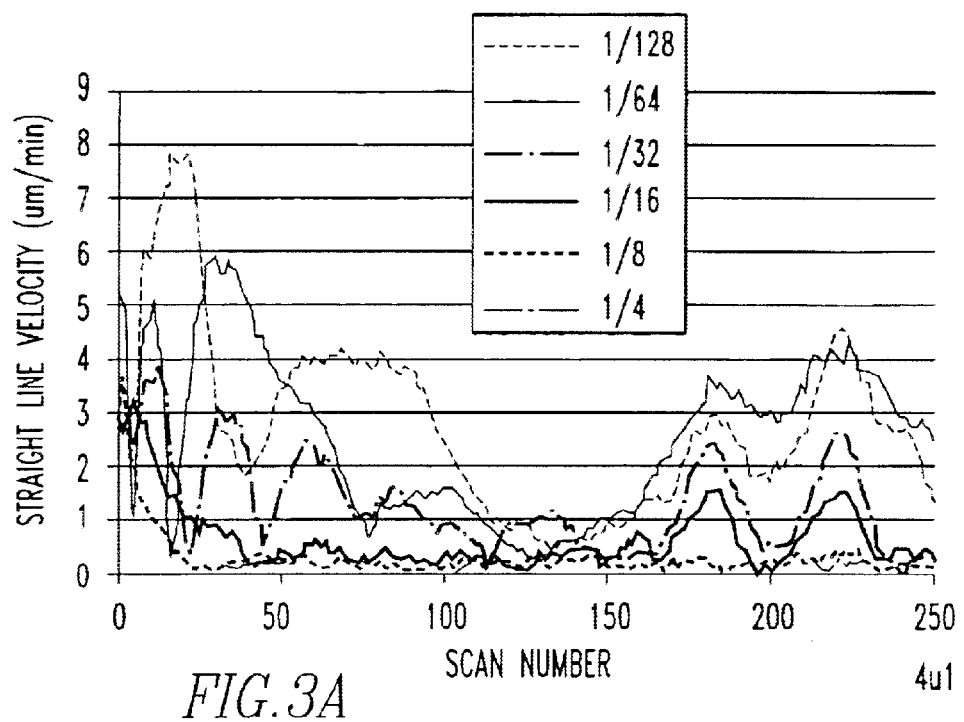
FIGS. 3a–3d show concentration of methyl cellulose for effective suppression of ambient motion.
Figure 3B:
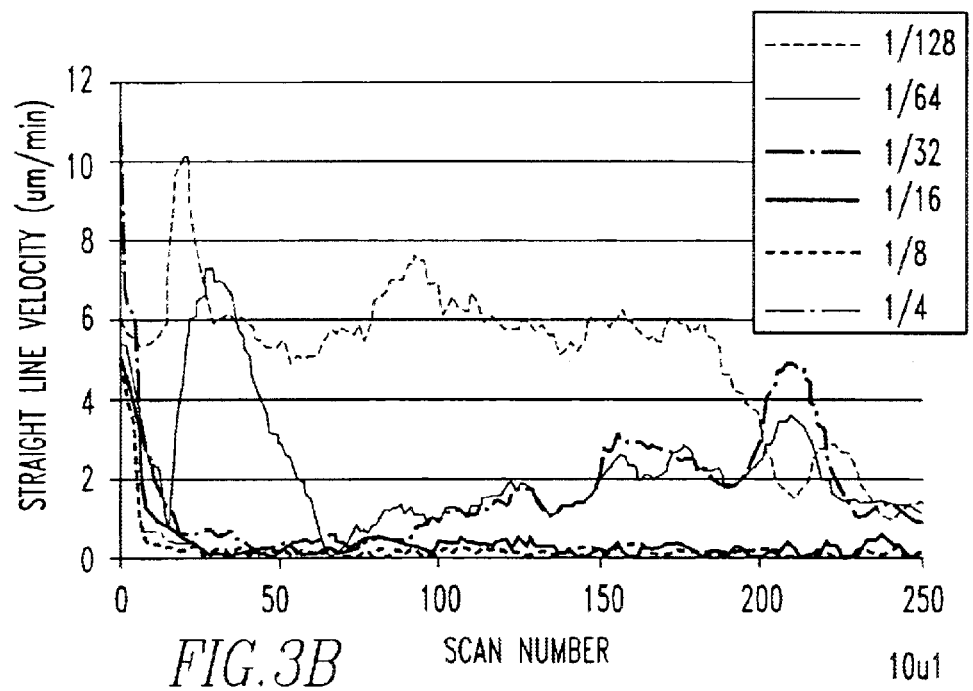
Figure 3C:
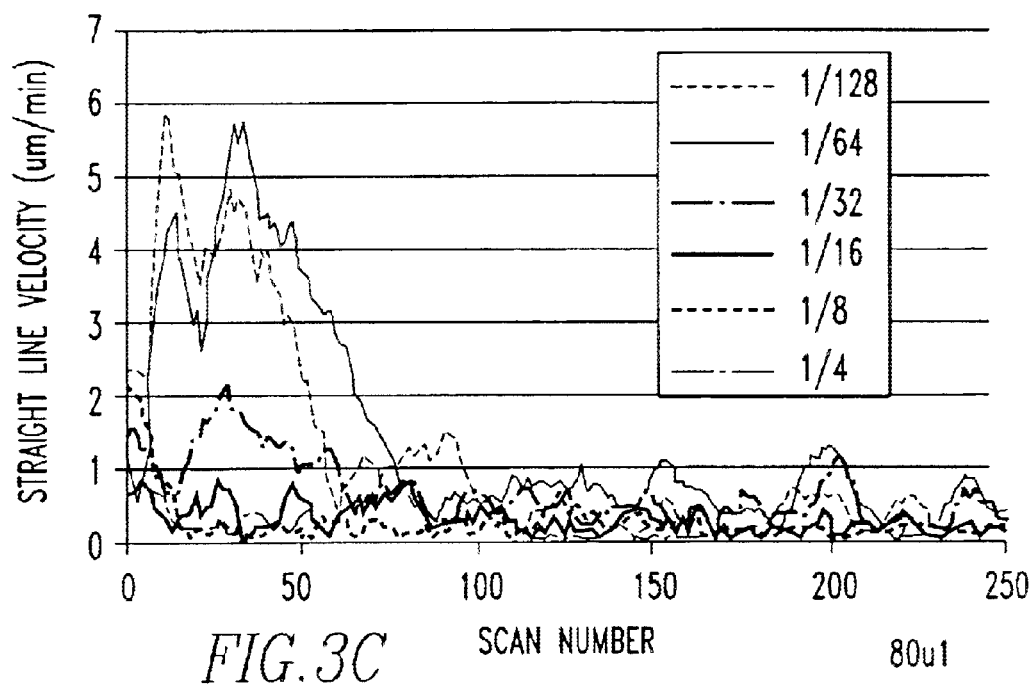
Figure 3D:
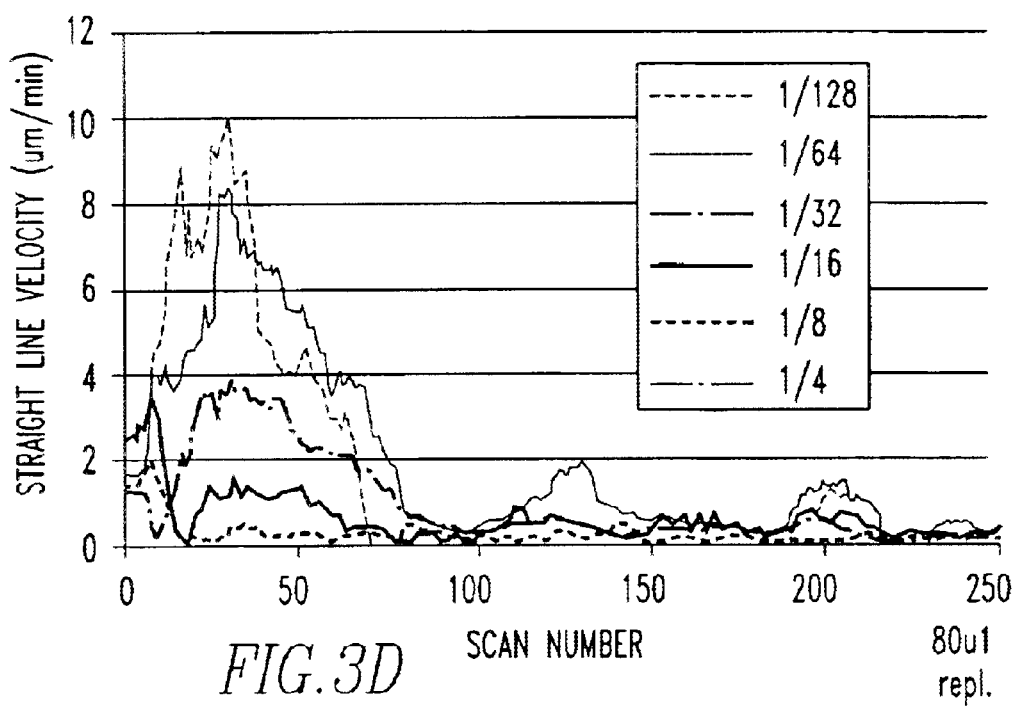

With a larger volume of 10 ul of methyl cellulose, the $\frac{1}{16}$ dilution level (0.08% methyl cellulose) is seen to be effective in preventing ambient motion throughout the 15 hour experimental time span, and a $\frac{1}{32}$ dilution (0.04% methyl cellulose) appears to show brief inhibition (FIG. 3B). The effectiveness of the $\frac{1}{16}$ dilution is further supported using 80 ul of the methyl cellulose dilution series added to T cells in 20 ul of complete medium. In this case, even homogenization with the overlying medium would not significantly alter the concentrations (FIG. 3C).

A separate experiment was designed to determine the minimum volume of methyl cellulose needed to suppress ambient motion. Volumes of 1, 2, 3, and 4 ul of stock solution (1.2% methyl cellulose) were added to wells containing 100 ul of complete medium in a 96 well plate. (For 384-well, 1536-well, and other plate sizes, corresponding volumes consist of approximately 1 to 4% of the total volumes of medium.) As in other experiments, suspended T cells were allowed to settle prior to methyl cellulose addition.

Figure 4A:
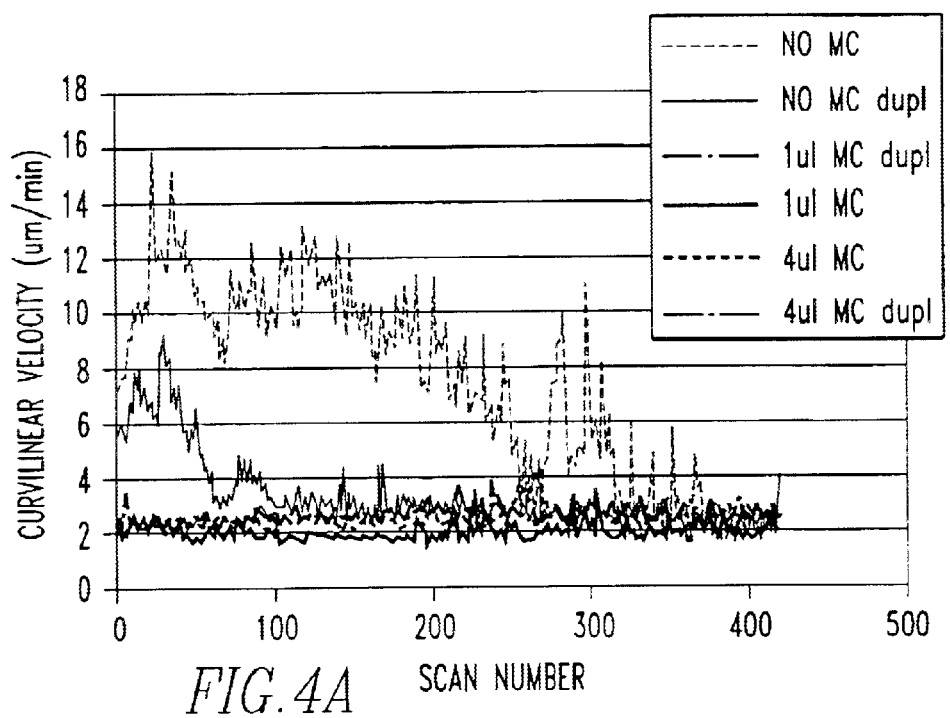
FIGS. 4a and 4b show volumes of 1 ul to 4 ul of full strength methyl cellulose stock are equally effective for suppression of ambient motion.

Results in terms of Vcl and Vsl (FIGS. 4A and 4B, respectively) show that volumes of 1 ul to 4 ul of ethyl cellulose stock (1.2% methyl cellulose) are equally effective for suppression of ambient motion. Methyl cellulose-containing samples at 1 ul, 2 ul, 3 ul, and 4 ul (Duplicates B and C05, 06, 07 and 08, respectively) were compared with duplicate samples without methyl cellulose (B04 and C04). Extreme ambient motion differs widely between duplicate samples without methyl cellulose, while all volumes of methyl cellulose are effective at allowing random motion (Vcl ~2 um/min, A-Top Panel) and suppressing ambient motion (Vsl ~0, B-Bottom Panel). As expected, duplicate wells without methyl cellulose show drastically elevated values for Vcl and Vsl in comparison to samples with methyl cellulose. Examination of Vsl indicates that a major portion of this velocity of tracked cells in this case is unidirectional. That is, since values for Vcl and Vsl are similar, most of the observed Vcl must be unidirectional for the samples without methyl cellulose.

On the other hand, for all 4 volumes of methyl cellulose in this experiment, comparison of plots for Vcl with those for Vsl indicates that most of the motion is random directional because Vsl values remain near zero throughout the period of analysis. Therefore for Vcl, average levels of 2 to 3 um/min represent biological motility. This conclusion is clearly evident in FIG. 5, where green lines indicate the path of tracked cells over a representative period of time during this experiment comparing cells in a typical well without methyl cellulose (left panel) with a well containing cells with a 1 ul volume of added methyl cellulose (right panel). Without methyl cellulose, cells are moving uniformly down to the right, whereas with 1 ul of methyl cellulose, cells are moving in random paths characteristic of biological motion. Here the tracks have been superimposed upon one viewfield image. Sequences of images of T cells were acquired every 2 minutes and were analyzed automatically using custom software. On the average throughout the period analyzed, there were about 170 cells per field, 40% of which were motile.

Figure 4B:
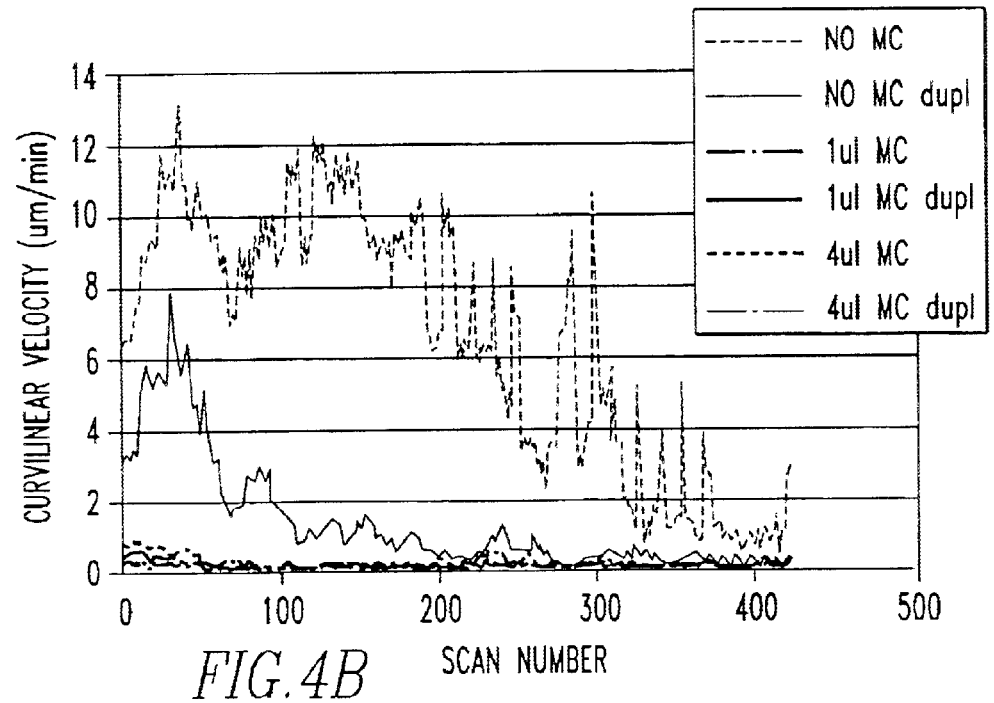
Figure 5A:
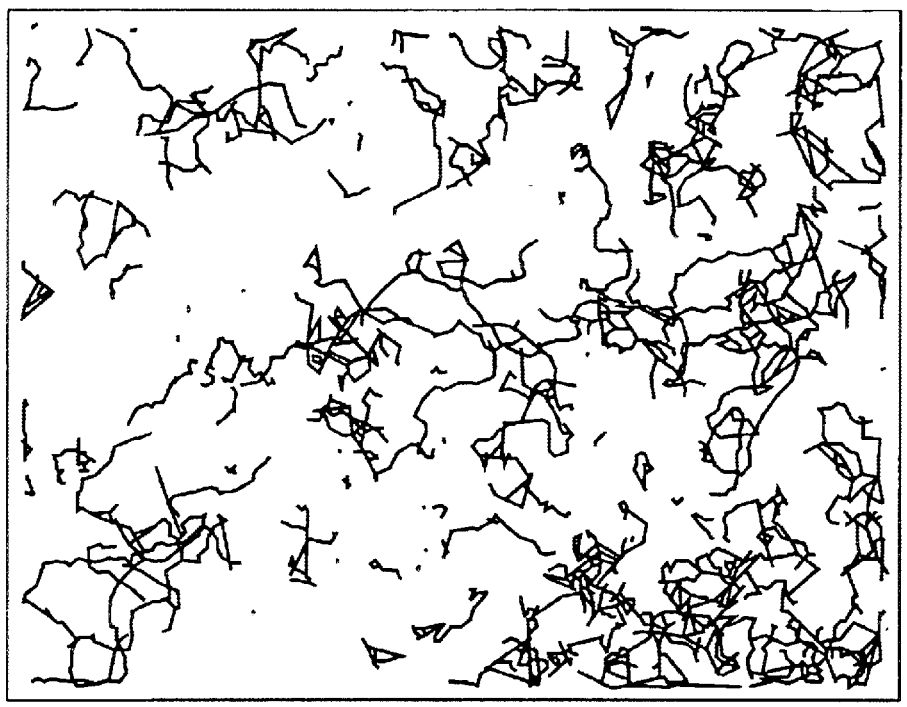
FIGS. 5a and 5b show T cell tracks in wells containing methyl cellulose and FIGS. 5c and 5d show T cell tracks without methyl cellulose indicating the path traveled by T cells over the course of analysis; ambient motion vs. random biological motion.
Figure 5B:
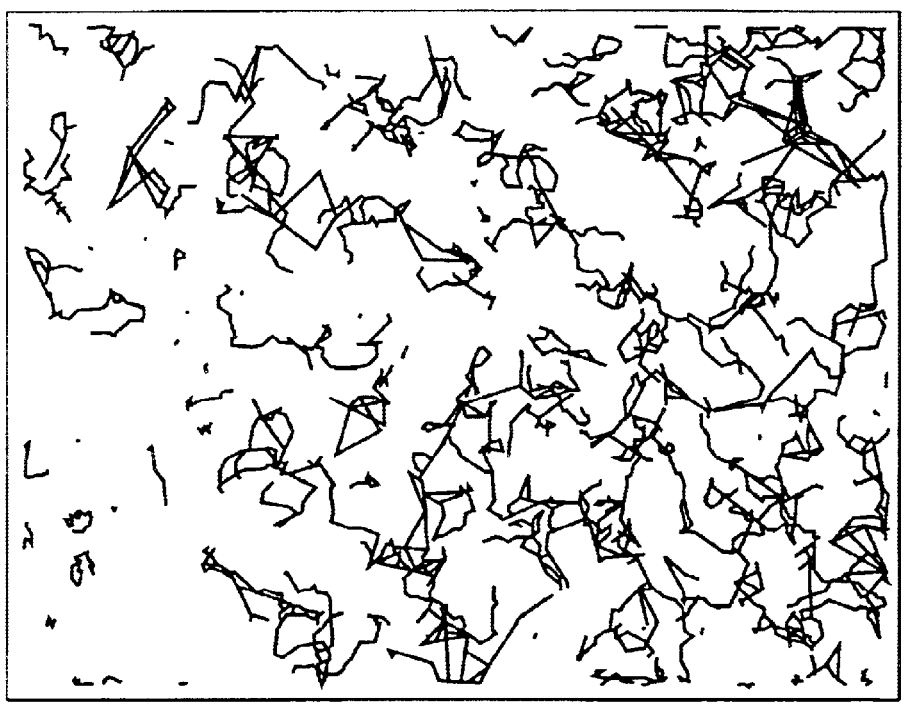
Figure 5C:
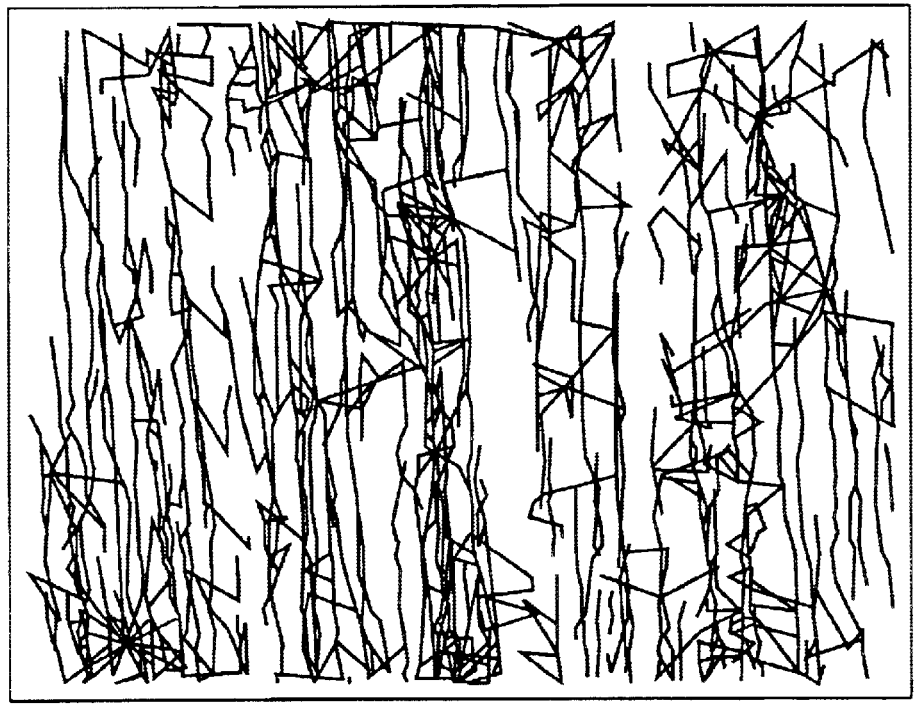
Figure 5D:
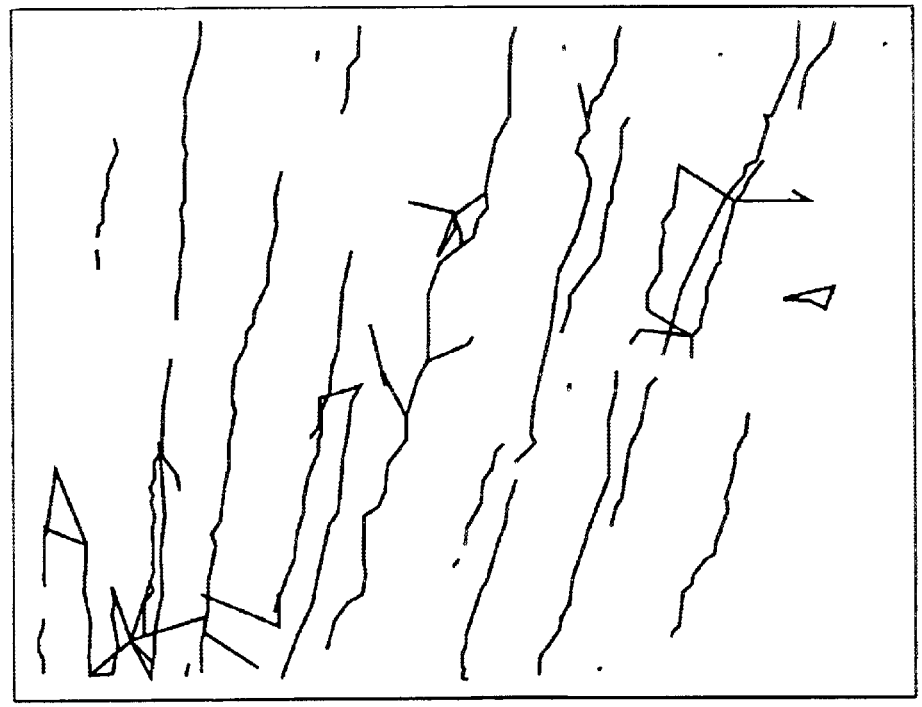

For one of the non-methyl cellulose-containing wells, the Vsl approaches zero halfway through the analysis period (FIG. 4B). For this sample, the average Vcl is practically identical in comparison to all of the methyl cellulose-containing wells (FIG. 4A), and thus in this example, T cell motility in complete medium is no different than T cell motility in the presence of full strength methyl cellulose stock solution (1.2% methyl cellulose) at volumes up to 4 ul. This example demonstrates no significant effect of methyl cellulose on T cell motility in comparison to motion in medium alone when ambient motion is not present.

The calculated height of the methyl cellulose layer using volumes from 1 to 4 ul in a 96 well plate is shown in Table 1.

TABLE 1

| Volume of methyl cellulose (ul) added to 100 ul medium | Height of methyl cellulose (um) |
|---|---|
| 0 | — |
| 1 | 34 |

TABLE 1-continued

| Volume of methyl cellulose (ul) added to 100 ul medium | Height of methyl cellulose (um) |
|---|---|
| 2 | 69 |
| 3 | 103 |
| 4 | 137 |

These data indicate that as little as 1 ul of full strength methyl cellulose is effective for suppression of ambient motion in 96 well plates and that greater precision may be expected for measurement of motility parameters due to reduced ambient motion using methyl cellulose.

Figure 6A:
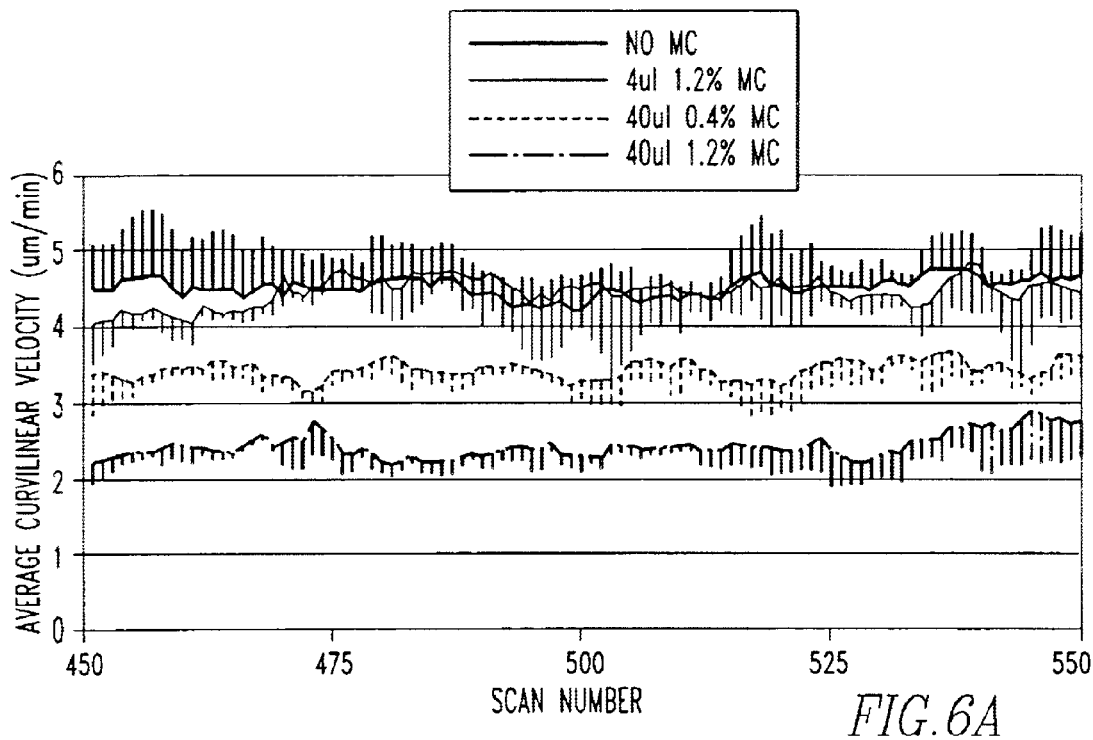
FIGS. 6a and 6b show the effect of large volume of methyl cellulose upon T cell motility characteristics.
Figure 6B:
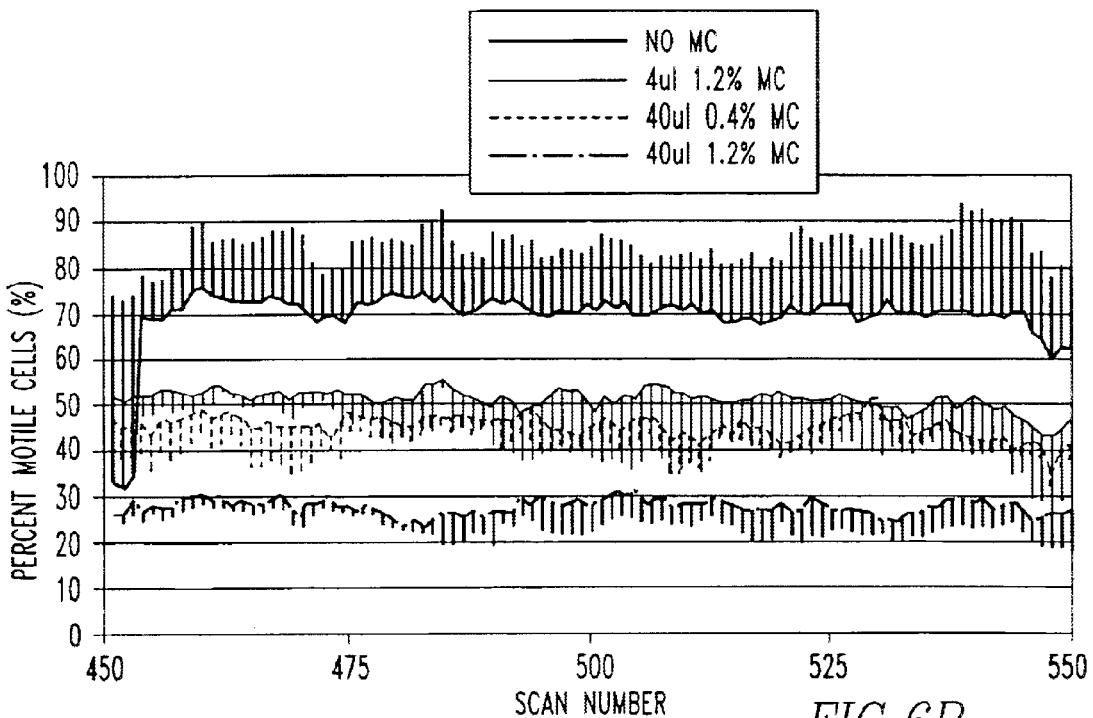

In an experiment designed to test for possible effects of methyl cellulose on T cell motility, 4 ul and 40 ul volumes of full strength (1.2%) methyl cellulose and 40 ul volumes of 1/3 diluted (0.4%) methyl cellulose were added to T cells in 96 well plates. Plots of curvilinear velocity (Vcl) are shown in FIG. 6. Although the 4 ul volume layer of full strength (1.2%) methyl cellulose shows similar T cell curvilinear velocity to the plastic without methyl cellulose (uppermost curves), 40 ul volumes of full strength (1.2% methyl cellulose) and diluted (⅓; 0.4% methyl cellulose) methyl cellulose show an apparent reduction in velocity in comparison to the 4 ul volume layer and plastic without methyl cellulose. Possible interpretations for this effect include the differing composition of methyl cellulose mixtures in comparison to complete medium, and the possibility that with larger volumes, T cells are deprived of factors and/or nutrients that are necessary for "normal" behavior. Also, when watching time-lapse sequences of images with 40 ul of full strength methyl cellulose, it is apparent that when cells move, they are capable of moving upwards vertically. They then go out of focus and out of view. Thus the more rapidly moving cells are being selected against in terms of cells that remain in the viewfield.

Figure 7D:
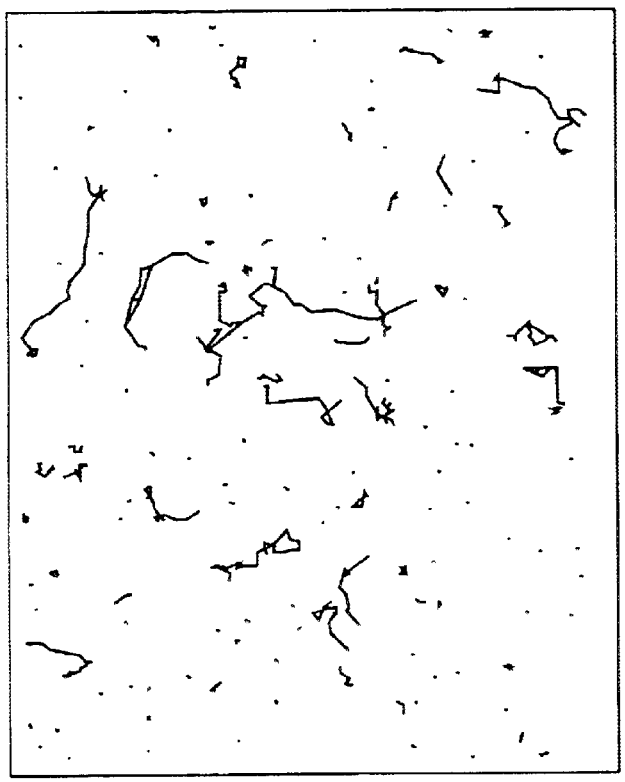
FIGS. 7c and 7d show view fields where cells remained in view with methyl cellulose present from the period over which the data were analyzed in FIG. 6.
Figure 7C:

FIG. 7 shows examples from this experiment of view fields analyzed, with the cell tracks represented by green lines. FIGS. 7 shows tracks of cells from the period over which the data were analyzed in FIG. 6. When methyl cellulose was not present (top two panels), cells were readily swept from the viewfield at different times; it was then possible for selected cells to replace them yielding fewer cells of higher motility than in viewfields with methyl cellulose (lower panels) where cells remained in view from the beginning and greater numbers of non-motile cells remained. In the case of 40 ul of non-diluted methyl cellulose (lower right panel), cells were observed to move in 3 dimensions, and so moving cells frequently left the viewfield as they went out-of-focus. These and other biases make it difficult to determine the extent to which methyl cellulose might affect T cell motility. Two wells without methyl cellulose (FIGS. 7A & B—plastic) present the extent of variation observed without methyl cellulose, whereas with methyl cellulose (FIGS. 7C & D), similar numbers of cells are distributed across the viewfield and these cells have remained from initial images. Tracks show similar lengths in FIG. 7C (40 ul diluted methyl cellulose) in comparison to FIG. 7B (plastic), however there are more stationary cells remaining in FIG. 7C; such cells having been swept out of the viewfield due to ambient motion in FIG. 7B. In FIG. 7D, many of the motile cells have escaped into the vertical direction and are therefore out-of-focus and not tracked. Further experiments with a dilution series of methyl cellulose may bring answers to the question of effects of methyl cellulose on T cell motility. In any case, it is evident that cell motion is not adversely affected by smaller volumes of methyl cellulose and that suppression of the otherwise dominant effects of ambient motion is required for measuring motility of non adherent cells.

The method and procedure of adding a small volume of methyl cellulose as a layer on top of settled cells leaves a relatively wide margin of approximately 0.1% to 1.2% methyl cellulose concentrations for effective inhibition of ambient motion. Alternatively, it is convenient and satisfactory to mix methyl cellulose homogeneously in solution with the cell culture medium in which the cells are suspended and allowed to settle. In this case the effective concentration range is restricted to approximately 0.1% to 0.2% for 2D analysis of motility. At concentrations lower than 0.1%, ambient motion is not sufficiently suppressed, and at concentrations higher than 0.2%, cells begin to migrate upwards from the surface into 3 dimensions. Analysis of motility in 3 dimensions is more complex than analysis in 2 dimensions. In 2 dimensions cells are imaged within a single plane of focus, whereas in 3 dimensions multiple focal planes must be imaged. Therefore 3D analysis must integrate the tracking of motion of objects between adjacent focal planes. Methyl cellulose provides considerable advantage in enabling 2D analysis of non-attachment mediated motility.

Figure 8A:
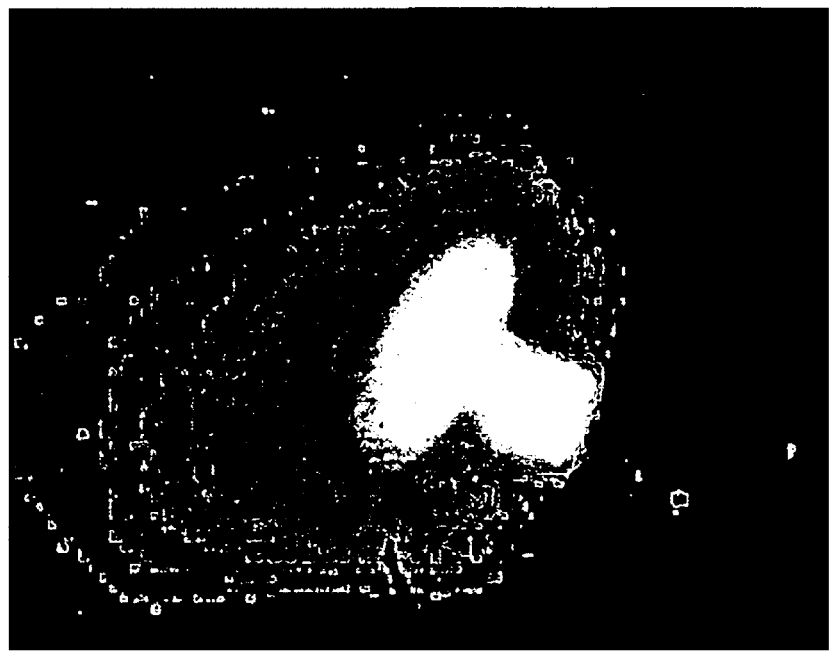
FIGS. 8a and 8b show a fluorescent image and a corresponding view in visible light, respectively.
Figure 8B:
Figure 8C:
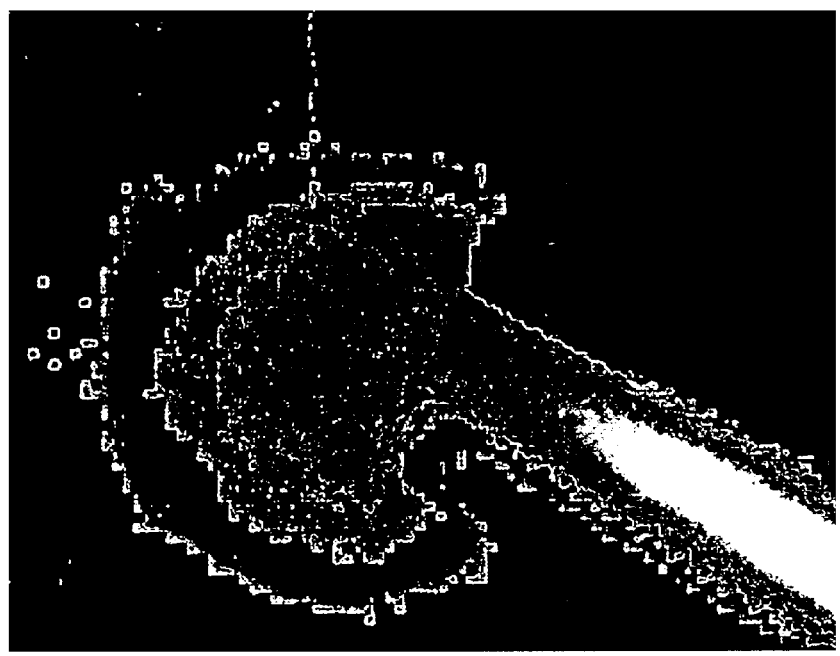
FIGS. 8c and 8d show a fluorescent image and a corresponding view in visible light, respectively.
Figure 8D:
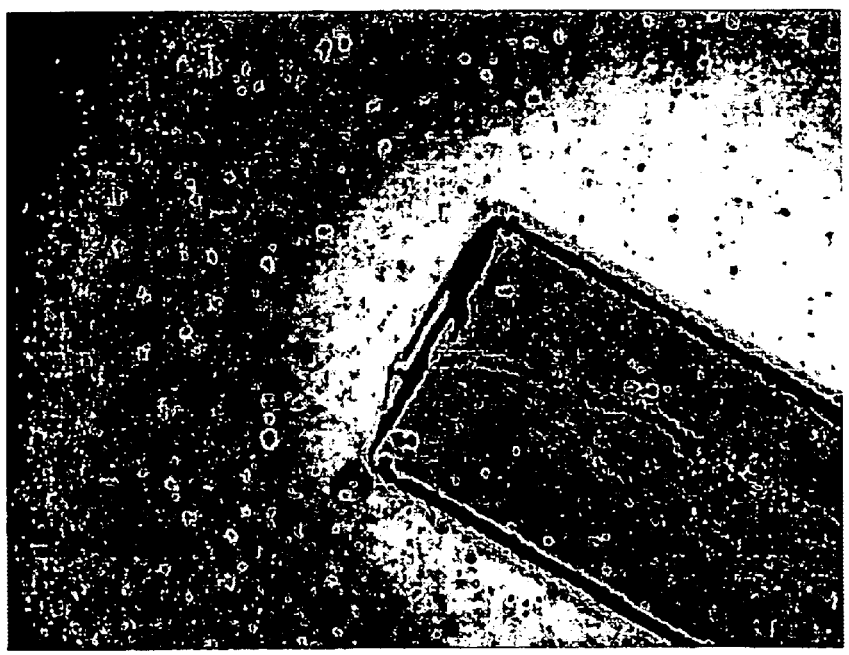

The addition of methyl cellulose to the culture medium is also an effective method for enabling the analysis of chemotaxis, or directional migration of cells toward an attractive compound. Chemcotaxis analysis is demonstrated by the establishment of chemical gradients as shown in FIGS. 8a–8d using fluorescent dye labeled dextran as markers. The left hand panels show fluorescent images and the right hand panels show the corresponding view in visible light. The dye markers, of 70 kilo-Dalton (kD) molecular weight (FIG. 8A) and 10 kD molecular weight (FIG. 8B), span a molecular weight range similar to that of bioactive chemotactic compounds, and provide a visual reference for gauging the slope and strength of the gradient of both the dyes and experimental nonvisible chemotactic compounds. In FIG. 8A, the dye may be seen to diffuse from within the impregnated semi-solid agarose gel held in place within a small cylinder of Teflon tubing (PTFE 0.047"OD× 0.015"ID). The agarose (Agarose GenAR, low gel temperature, cat# 7720, Mallinckrodt) contained within the tubing is approximately 1% concentration and the dyes consist of Oregon Green 488 conjugated dextran (70 kd cat# D-7173; 10 kd cat# D-7171, Molecular Probles) at approximately 1 mg/ml concentration in the gel dissolved in Dulbecco's phosphate buffered saline (DPBS cat# 14190-144, GibcoBRL).

In FIG. 8A it is evident that the agarose "plug" within the hollow cylinder of tubing is confined to the left-hand side of the lumen and that a small air bubble effectively blocks the right side (compare fluorescent image (8A—left) with visible image (8A—right)). Based on this observation, the tubing in FIG. 8B was created so that the agarose plug was positioned at the far right end (out of view) and was intentionally "capped" on this side with a small bubble of air (out of view). The left-hand side of the tube was filled with culture medium containing methyl cellulose similar in strength (approximately 0.8% methyl cellulose) to that in which the cells were suspended within the well. This configuration provides a method to slow the rate of diffusion from the tube opening in comparison to cutting the tube flush with the gel. Moreover, since the cells are capable of migrating in 3 dimensions in 0.8% methyl cellulose, the open section of tubing filled with methyl cellulose-containing culture medium supports migrating cells and creates a trap for chemotactic cells migrating upwards into the chemotactic gradient using 3D motility analysis methods.

Analysis for both attractive and repulsive interactions on cells from chemotactic gradients would be performed using either 2D or 3D motility analysis by comparison of the magnitude and direction of the cell migration vector field with that of the chemical gradient.

U.S. Pat. No. 6,008,010, incorporated by reference herein, describes a system that can also be used to perform the embodiments described herein.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method for analyzing an animal cell having an average curvilinear velocity of less than 8 $\mu$m/min by suppressing movement of the cell caused by other than activity of the cell itself comprising the steps of:
   placing the cell having a viscosity of about 100–5000 centipoises in a solution; and
   measuring the motility of the cell in the solution.

2. A method as described in claim 1 wherein the solution comprises methyl cellulose.

3. A method as described in claim 1 wherein the solution comprises hyaluronic acid or chondroitin sulfate or cellulose ester or polysaccharide.

4. A method as described in claim 1 wherein multiple cells are measured in parallel.

5. A method as described in claim 1 wherein the placing step includes the step of placing cells in solution having a concentration of between 0.3% to 2.5% weight per volume methyl cellulose for analysis of motility in 3D.

6. A method as described in claim 1 wherein the placing step includes the step of placing the cell in the solution of between 1% to 5% by total volume of methyl cellulose and a concentration of between 0.08% and 0.12% of methyl cellulose.

7. A method for analyzing an animal cell having an average curvilinear velocity of less than 8 um/min by suppressing movement of the cell caused by other than activity of the cell itself comprising the steps of:
   placing the cell having an average curvilinear velocity of less than 8 $\mu$m/min in a solution having a viscosity of about 100–5000 centipoises; and
   measuring the motility of the cell in the solution when there is no attachment of the cell to any surface involved.

8. A method for analyzing an animal cell having an average curvilinear velocity of less than 8 um/min comprising the steps of:
   placing the cell in a solution having a viscosity of about 100–5000 centipoise; and
   performing two-dimensional or three-dimensional migration analysis on the cell in the solution.

9. A method for analyzing an animal cell having an average curvilinear velocity of less than 8 um/min comprising the steps of:
   placing the cell in a solution having a viscosity of about 100–5000 centipoise; and
   analyzing migration of the cell in the solution which occurs without adherence of the cell to any surface.

10. A method for analyzing an animal cell having an average curvilinear velocity of less than 8 um/min comprising the steps of:
    placing the cell in a solution having a viscosity of about 100–5000 centipoise; and
    measuring motility of the cell in the solution, where surface attachment by the cell to any surface is not utilized.

11. A method for analyzing an animal cell having an average curvilinear velocity of less than 8 um/min by suppressing movement of the cell caused by other than activity of the cell itself comprising the steps of:
    placing the cell in a solution; and
    introducing methyl cellulose in the solution so that the solution has a viscosity of about 100–5000 centipoises to reduce ambient motion of the cell in the solution and eliminate convective motion.

12. A method for analyzing an animal cell having an average curvilinear velocity of less than 8 um/min by suppressing movement of the cell caused by other than activity of the cell itself comprising the steps of:
    placing the cell in a solution; and
    introducing methyl cellulose in the solution so that the solution has a viscosity of about 100–5000 centipoises to reduce or eliminate the effects of micro-turbulances due to thermal convection in the solution.

13. A method for analyzing an animal cell having an average curvilinear velocity of less than 8 um/min comprising the steps of:
    placing the cell in a solution; and
    introducing methyl cellulose in the solution so that the solution has a viscosity of about 100–5000 centipoises to stop of the cell due to movement of the solution induced by mechanical movement of a plate on which the cells are disposed.

14. A method for analyzing an animal cell having an average curvilinear velocity of less than 8 um/min comprising the steps of:
    placing the cell in a solution; and
    introducing a viscous fluid in the solution so that the solution has viscosity of about 100–5000 centipoises to stop or reduce the effects of gravity on the cell.

15. A method for analyzing an animal cell having an average curvilinear velocity of less than 8 um/min comprising the steps of:
    placing the cell in a solution; and
    introducing a viscous fluid in the solution so that the solution has viscosity of about 100–5000 centipoises to reduce the effects of micro-turbulences due to thermal convection.

16. A method for analyzing an animal cell having an average curvilinear velocity of less than 8 um/min comprising the steps of:
    placing the cell in a solution having a viscosity of about 100–5000 centipoises; and
    introducing a viscous fluid in the solution so that the solution has viscosity of about 100–5000 centipoises to stop motion of the cell due to effects on the cell of currents in the solution that are induced by motion of a plate on which the cell is disposed.

17. A method for analyzing either a T-cell, dendritic cell, B-cell or lymphocyte having an average straight line velocity of between 0 and 10 $\mu$m/min by suppressing movement of either a T-cell, dendritic cell, B-cell or lymphocyte caused by other than activity of either a T-cell, dendritic cell, B-cell or lymphocyte itself comprising the steps of:

placing the T-cell, dendritic cell, B-cell or lymphocyte in a solution having a viscosity of about 100–5000 centipoises; and measuring the motility of either a T-cell, dendritic cell, B-cell or lymphocyte in the solution.

18. A method for analyzing an animal cell having an average curvilinear velocity of less than 8 m/min by suppressing movement of the cell caused by other than activity of the cell itself comprising the steps of:

placing the cell in a solution of between 0.1% and 0.2% by total volume of methyl cellulose for 2D analysis of motility; and measuring the motility of the cell in the solution.

19. A method for analyzing an animal cell having an average curvilinear velocity of less than 8 m/mm by suppressing movement of the cell caused by other than activity of the cell itself comprising the steps of:

placing the cell in a solution of between 0.1% and 0.2% by total volume of methyl cellulose onto cells in culture medium to provide a layer of methyl cellulose-containing medium for 2D analysis of motility; and measuring the motility of the cell in the solution.

20. A method as described in any one of claims 7, 8, 9, 10, 11, and 12–16, and 17–19, wherein the animal cell is a human cell.

* * * * *